United States Patent
Novak et al.

(10) Patent No.: US 8,211,112 B2
(45) Date of Patent: Jul. 3, 2012

(54) MULTI-PART IMPLANT FOR OPEN WEDGE KNEE OSTEOTOMIES

(75) Inventors: Vincent P. Novak, Longmont, CO (US); Kelly Ammann, Boulder, CO (US)

(73) Assignee: Arthrex, Inc., Naples, FL (US)

( * ) Notice: Subject to any disclaimer, the term of this patent is extended or adjusted under 35 U.S.C. 154(b) by 958 days.

(21) Appl. No.: 11/352,103

(22) Filed: Feb. 9, 2006

(65) Prior Publication Data

US 2006/0217808 A1   Sep. 28, 2006

Related U.S. Application Data

(63) Continuation-in-part of application No. 11/047,159, filed on Jan. 31, 2005, and a continuation-in-part of application No. 11/047,551, filed on Jan. 31, 2005, now Pat. No. 8,083,746.

(60) Provisional application No. 60/651,304, filed on Feb. 9, 2005.

(51) Int. Cl.
*A61F 5/00* (2006.01)

(52) U.S. Cl. .................................................. 606/87

(58) Field of Classification Search ............ 606/87–89; 623/13.12, 16.11, 20.14, 20.15, 17.11–17.16
See application file for complete search history.

(56) References Cited

U.S. PATENT DOCUMENTS

| | | |
|---|---|---|
| 2,737,724 A | 3/1956 | Herz |
| 3,579,777 A | 5/1971 | Milewski |
| 3,750,652 A | 8/1973 | Sherwin |
| 4,349,018 A | 9/1982 | Chambers |
| 4,421,112 A | 12/1983 | Mains et al. |
| 4,501,268 A | 2/1985 | Comparetto |
| 4,523,587 A | 6/1985 | Frey |
| 4,563,489 A | 1/1986 | Urist |
| 4,565,191 A | 1/1986 | Slocum |
| 4,750,481 A | 6/1988 | Reese |
| 4,769,040 A | 9/1988 | Wevers |
| 4,817,794 A | 4/1989 | Workman |
| 4,851,005 A | 7/1989 | Hunt et al. |
| 4,852,558 A | 8/1989 | Outerbridge |
| 4,892,093 A | 1/1990 | Zarnowski et al. |
| 4,936,844 A | 6/1990 | Chandler et al. |
| 4,961,740 A | 10/1990 | Ray et al. |
| 5,053,039 A | 10/1991 | Hofmann et al. |
| 5,254,119 A | 10/1993 | Schreiber |

(Continued)

FOREIGN PATENT DOCUMENTS

CN   1132067   10/1996

(Continued)

OTHER PUBLICATIONS

Oliver C. Kessler et al., Avoidance of Medial Cortical Fracture in High Tibial Osteotomy: Improved Technique, Clinical Orthopaedics and Related Research, Feb. 2002, pp. 180-185, No. 395.

(Continued)

*Primary Examiner* — Eduardo C Robert
*Assistant Examiner* — Jacqueline Johanas
(74) *Attorney, Agent, or Firm* — Dickstein Shapiro LLP

(57) ABSTRACT

An osteotomy implant for supporting an open wedge osteotomy and method of use are described. In one form, the implant is configured to contain a graft material within the osteotomy. In another form, the implant is composed of multiple parts capable of being assembled either before or after insertion into the osteotomy.

25 Claims, 34 Drawing Sheets

U.S. PATENT DOCUMENTS

| | | | |
|---|---|---|---|
| 5,275,603 A | 1/1994 | Ferrante et al. | |
| 5,297,538 A | 3/1994 | Daniel | |
| 5,306,276 A | 4/1994 | Johnson et al. | |
| 5,352,229 A | 10/1994 | Goble et al. | |
| 5,413,579 A | 5/1995 | Du Toit | |
| 5,445,640 A | 8/1995 | Johnson et al. | |
| 5,451,228 A | 9/1995 | Johnson et al. | |
| 5,540,695 A | 7/1996 | Levy | |
| 5,569,250 A | 10/1996 | Sarver et al. | |
| 5,601,565 A | 2/1997 | Huebner | |
| 5,609,635 A | 3/1997 | Michelson | |
| 5,613,969 A | 3/1997 | Jenkins, Jr. | |
| 5,620,448 A | 4/1997 | Puddu | |
| 5,640,813 A | 6/1997 | Glazik et al. | |
| 5,662,655 A | 9/1997 | Laboureau et al. | |
| 5,669,909 A | 9/1997 | Zdeblick et al. | |
| 5,674,296 A | 10/1997 | Bryan et al. | |
| 5,681,316 A | 10/1997 | DeOrio et al. | |
| 5,722,978 A | 3/1998 | Jenkins, Jr. | |
| 5,733,290 A | 3/1998 | McCue et al. | |
| 5,749,875 A | 5/1998 | Puddu | |
| 5,766,251 A * | 6/1998 | Koshino | 623/11.11 |
| 5,843,085 A | 12/1998 | Graser | |
| 5,888,223 A | 3/1999 | Bray, Jr. | |
| 5,911,724 A | 6/1999 | Wehrli | |
| 5,980,526 A | 11/1999 | Johnson et al. | |
| 6,008,433 A | 12/1999 | Stone | |
| 6,027,504 A | 2/2000 | McGuire | |
| 6,039,761 A | 3/2000 | Li et al. | |
| 6,086,593 A | 7/2000 | Bonutti | |
| 6,099,531 A | 8/2000 | Bonutti | |
| 6,102,950 A | 8/2000 | Vaccaro | |
| 6,190,390 B1 | 2/2001 | McAllister | |
| 6,200,347 B1 | 3/2001 | Anderson et al. | |
| 6,203,546 B1 | 3/2001 | MacMahon | |
| 6,214,007 B1 | 4/2001 | Anderson | |
| 6,224,599 B1 * | 5/2001 | Baynham et al. | 606/90 |
| 6,264,694 B1 | 7/2001 | Weiler | |
| 6,277,149 B1 | 8/2001 | Boyle et al. | |
| 6,287,308 B1 | 9/2001 | Betz et al. | |
| 6,379,361 B1 | 4/2002 | Beck, Jr. et al. | |
| 6,423,063 B1 | 7/2002 | Bonutti | |
| 6,461,359 B1 | 10/2002 | Tribus et al. | |
| 6,478,800 B1 | 11/2002 | Fraser et al. | |
| 6,565,570 B2 | 5/2003 | Sterett et al. | |
| 6,575,982 B1 | 6/2003 | Bonutti | |
| 6,648,917 B2 * | 11/2003 | Gerbec et al. | 623/17.11 |
| 6,699,252 B2 | 3/2004 | Farr, II et al. | |
| 6,743,255 B2 | 6/2004 | Ferree | |
| 6,755,841 B2 | 6/2004 | Fraser et al. | |
| 6,796,986 B2 | 9/2004 | Duffner | |
| 6,823,871 B2 | 11/2004 | Schmieding | |
| 2002/0010513 A1 | 1/2002 | Schmieding | |
| 2002/0029084 A1 | 3/2002 | Paul et al. | |
| 2002/0095156 A1 | 7/2002 | Kuras et al. | |
| 2002/0165552 A1 * | 11/2002 | Duffner | 606/87 |
| 2003/0028197 A1 | 2/2003 | Hanson et al. | |
| 2003/0040799 A1 * | 2/2003 | Boyd et al. | 623/17.11 |
| 2003/0105526 A1 * | 6/2003 | Bryant et al. | 623/16.11 |
| 2003/0171757 A1 | 9/2003 | Coon et al. | |
| 2003/0195516 A1 | 10/2003 | Sterett et al. | |
| 2003/0199881 A1 | 10/2003 | Bonutti | |
| 2004/0034430 A1 * | 2/2004 | Falahee | 623/17.16 |
| 2004/0039387 A1 | 2/2004 | Gause et al. | |
| 2004/0153072 A1 * | 8/2004 | Bonutti | 606/61 |
| 2004/0254644 A1 * | 12/2004 | Taylor | 623/17.13 |
| 2004/0267366 A1 * | 12/2004 | Kruger | 623/17.16 |
| 2005/0075641 A1 * | 4/2005 | Singhatat et al. | 606/86 |
| 2005/0177245 A1 * | 8/2005 | Leatherbury et al. | 623/23.5 |
| 2005/0216090 A1 | 9/2005 | O'Driscoll et al. | |
| 2005/0228498 A1 | 10/2005 | Andres | |
| 2005/0240267 A1 * | 10/2005 | Randall et al. | 623/17.11 |
| 2005/0251147 A1 | 11/2005 | Novak | |
| 2005/0273114 A1 | 12/2005 | Novak | |
| 2005/0273115 A1 | 12/2005 | Coon et al. | |
| 2006/0106396 A1 | 5/2006 | Justin et al. | |
| 2006/0122617 A1 | 6/2006 | Lavallee et al. | |
| 2006/0129163 A1 | 6/2006 | McGuire | |
| 2006/0149274 A1 | 7/2006 | Justin et al. | |
| 2006/0149275 A1 | 7/2006 | Cadmus | |
| 2006/0241636 A1 | 10/2006 | Novak et al. | |
| 2007/0016209 A1 | 1/2007 | Ammann et al. | |
| 2009/0132046 A1 * | 5/2009 | Larche | 623/14.12 |

FOREIGN PATENT DOCUMENTS

| | | |
|---|---|---|
| CN | 1181696 | 5/1998 |
| EP | 1669033 | 6/2006 |
| FR | 2741525 | 5/1997 |
| WO | WO 2005/048888 | 6/2005 |
| WO | WO 2006/107800 | 10/2006 |

OTHER PUBLICATIONS

David H. Sohn et al., Meniscus Transplantation: Current Concepts, The Journal of Knee Surgery, Apr. 2008, pp. 163-172, vol. 21, No. 2.

* cited by examiner

MULTI-PART IMPLANT FOR OPEN WEDGE KNEE OSTEOTOMIES

REFERENCE TO PENDING PRIOR PATENT APPLICATIONS

This patent application:

(i) is a continuation-in-part of pending prior U.S. patent application Ser. No. 11/047,159, filed Jan. 31, 2005 by Vincent P. Novak for OPEN WEDGE OSTEOTOMY SYSTEM AND SURGICAL METHOD;

(ii) is a continuation-in-part of prior U.S. patent application Ser. No. 11/047,551, now U.S. Pat. No. 8,083,746 filed Jan. 31, 2005 by Vincent P. Novak for OPEN WEDGE OSTEOTOMY SYSTEM AND SURGICAL METHOD; and (iii) claims benefit of pending prior U.S. Provisional Patent Application Ser. No. 60/651,304, filed Feb. 9, 2005 by Vincent P. Novak et al. for OPEN WEDGE OSTEOTOMY SYSTEM AND SURGICAL METHOD.

The three above-identified patent applications are hereby incorporated herein by reference.

FIELD OF THE INVENTION

This invention relates to surgical methods and apparatus in general, and more particularly to surgical methods and apparatus for performing open wedge osteotomies of the knee.

BACKGROUND OF THE INVENTION

Osteotomies of the knee are an important technique for treating knee osteoarthritis. In essence, knee osteotomies adjust the geometry of the knee joint so as to transfer weight bearing load from arthritic portions of the joint to the relatively unaffected portions of the joint.

Most knee osteotomies are designed to modify the geometry of the upper tibia, so as to adjust the manner in which the tibia engages the femur and hence the locations at which the load is transferred across the joint.

There are essentially two ways in which to adjust the orientation of the tibia: (i) the closed wedge technique; and (ii) the open wedge technique.

With the closed wedge technique, a wedge of bone is removed from the tibia, and the portions on either side of the resulting gap are brought together, whereby to reorient the tibial plateau and hence adjust the manner in which the tibia engages the femur.

With the open wedge technique, a cut is made into the tibia, the portions on either side of the cut are moved apart so as to form a wedge-like opening in the bone, and then the bone is secured in this position (e.g., by screwing metal plates to the bone or by inserting a wedge-shaped implant into the opening in the bone), whereby to reorient the tibial plateau and hence adjust the manner in which the tibia engages the femur.

While both closed wedge osteotomies and open wedge osteotomies provide substantial benefits to the patient, they are procedurally challenging to the surgeon. Furthermore, with respect to open wedge osteotomies, the wedge-shaped implants currently used are relatively large and awkward to position, and do not lend themselves to minimally invasive procedures, among other things.

The present invention is directed to open wedge osteotomies, and to wedge-shaped implants for positioning in the osteotomy opening.

SUMMARY OF THE INVENTION

The present invention comprises a novel method and apparatus for effecting an open wedge osteotomy. More particularly, the present invention comprises the provision and use of a novel multi-part implant for use in an open wedge osteotomy.

In one form of the present invention, there is provided an osteotomy implant for supporting an open wedge osteotomy, the osteotomy implant comprising:

a first graft containment arm for disposition along one side of the open wedge osteotomy;

a second graft containment arm for disposition along a second, opposite side of the open wedge osteotomy; and a base component for disposition along the mouth of the open wedge osteotomy, the base component being configured to selectively connect the first graft containment arm and the second graft containment arm to one another so as to form a generally wedge-shaped structure, wherein the base component constitutes the thicker end of the wedge.

In another form of the present invention, there is provided a method for conducting an open wedge osteotomy, comprising:

forming a wedge-like opening in the bone;

positioning a first graft containment arm along one side of the wedge-like opening, and positioning a second graft containment arm along a second, opposite side of the wedge-like opening; and positioning a base component along the mouth of the wedge-like opening, the base component being selectively connected to the first graft containment arm and the second graft containment arm so as to form a generally wedge-shaped structure, wherein the base component constitutes the thicker end of the wedge.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Forming the Wedge-Like Opening in the Tibia

Figure 1:
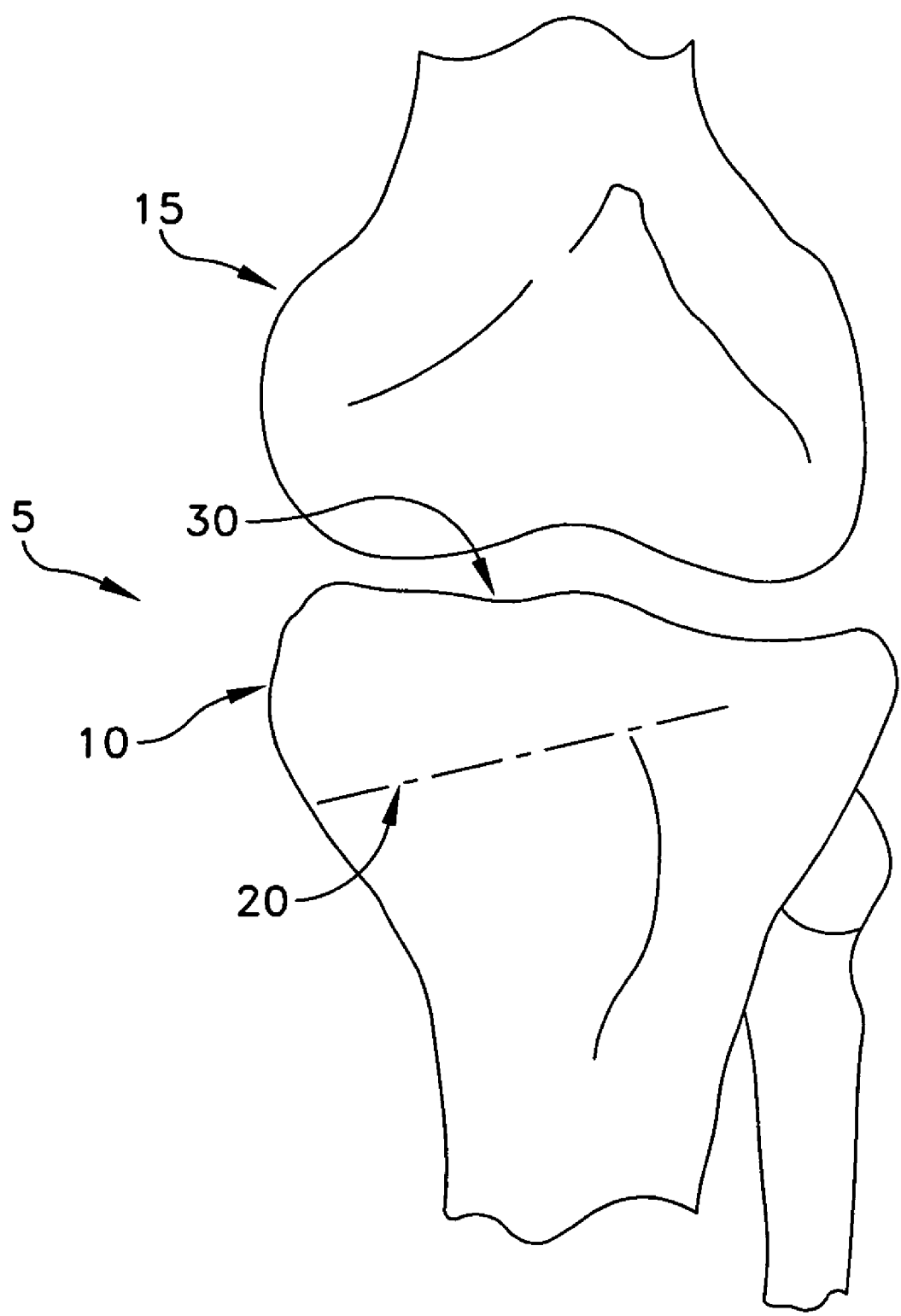
FIGS. 1 and 2 are schematic views showing the formation of the wedge-like opening in the tibia for an open wedge osteotomy.
Figure 2:
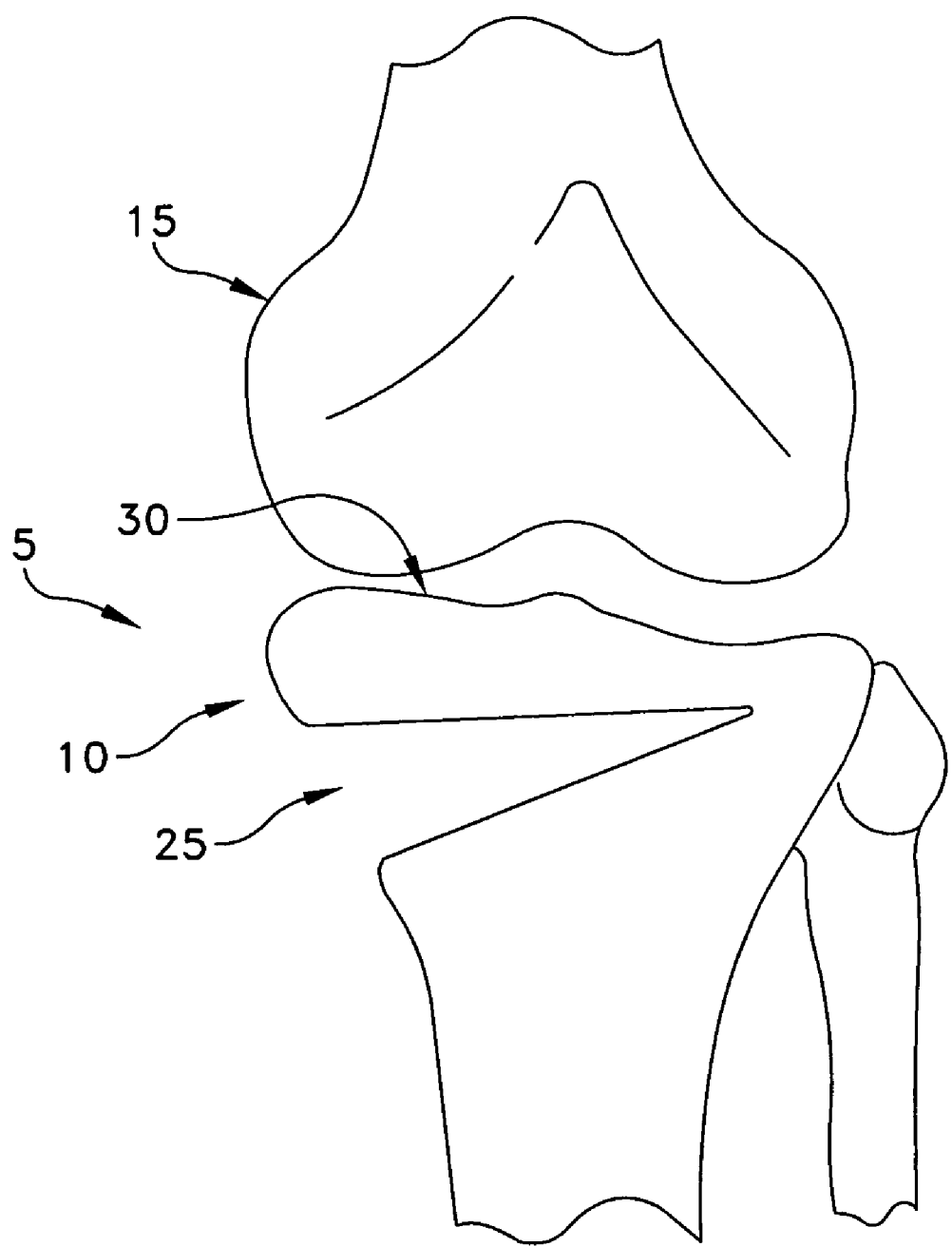

Looking first at FIGS. 1 and 2, there is shown a knee joint 5 upon which an open wedge osteotomy is to be performed. Knee joint 5 generally comprises a tibia 10 and a femur 15. In accordance with the present invention, the open wedge osteotomy is effected by first making a cut 20 (FIG. 1) into the upper tibia, and then moving apart the portions of the bone on either side of cut 20 so as to form a wedge-like opening 25 (FIG. 2) in the bone, with the wedge-like opening 25 being configured such that the tibial plateau 30 is given the desired orientation relative to femur 15. Cut 20 and wedge-like opening 25 may be formed in a variety of ways well known in the art. In one preferred form of the invention, cut 20 and wedge-like opening 25 are formed using an antero-medial approach, preferably with a minimally invasive technique.

In accordance with the present invention, once the desired wedge-like opening 25 has been formed in tibia 10 and tibial plateau 30 given its desired orientation, a novel multi-part implant is positioned in wedge-like opening 25 so as to maintain the reconfigured geometry of the tibia while weight bearing load is applied and healing occurs.

The Novel Multi-Part Implant in General

In accordance with the present invention, the novel implant comprises a multi-part construction having a generally wedge-shaped configuration substantially corresponding to the geometry of the wedge-shaped opening 25. The various components of the multi-part implant are intended to be assembled together, preferably in-situ, so as to form the complete wedge-shaped implant. The multi-part construction of the implant is significant and provides numerous advantages over prior art implants.

First, the multi-part construction permits patient-specific sizing of the implant with reduced inventory requirements. In addition, if desired, the implant can be trimmed on-site, in the operating room, to even more precisely approximate the geometry of wedge-shaped opening 25.

Second, the multi-part construction of the new implant permits the various component parts to be separately introduced into wedge-shaped opening 25, with the parts thereafter being connected together so as to form the complete implant. Since each of the component parts is relatively small, they are easy to manipulate and, as such, can be more precisely placed in position.

Third, the multi-part approach facilitates use of the implant with minimally invasive procedures.

Multi-Part Implant with Tab and Slot Interface Construction

Figure 3:
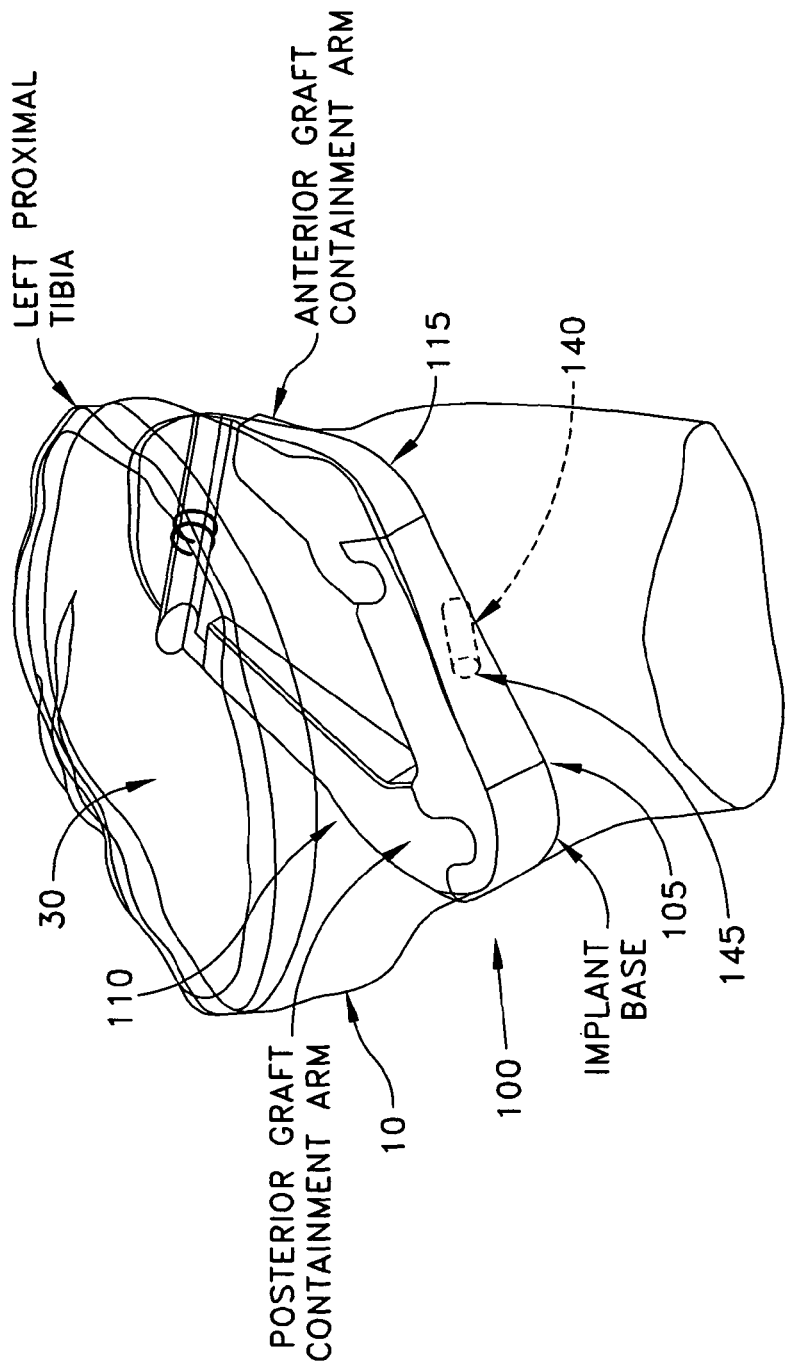
FIGS. 3-10 are schematic views showing various multi-part implants with tab and slot interface construction.
Figure 4:
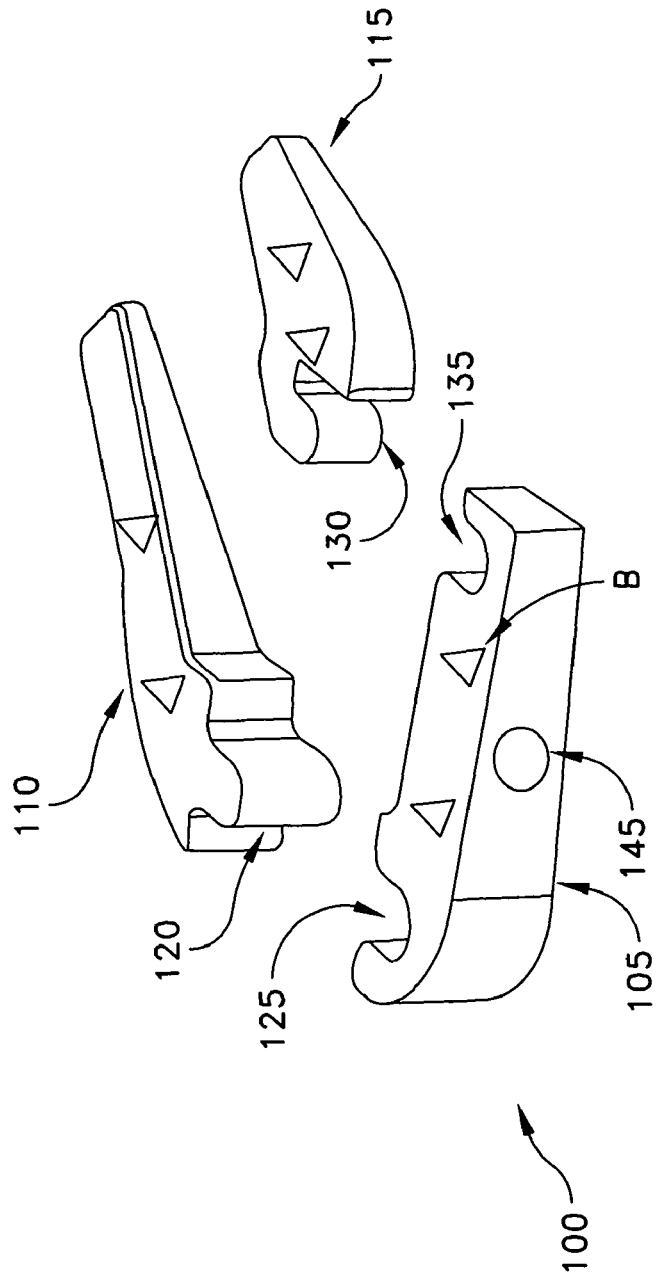

Looking next at FIGS. 3 and 4, in one preferred form of the invention, there is provided a novel implant 100 which generally comprises a base 105, a first graft containment arm 110 and a second graft containment arm 115. Base 105, first graft containment arm 110 and second graft containment arm 115 are intended to be attached together, preferably in-situ, so as to collectively form a generally wedge-shaped structure, with base 105 constituting the thicker end of the wedge. In the case where wedge-shaped opening 25 is formed using an antero-medial approach (e.g., such as that shown in FIG. 3), so that implant 100 is positioned using an antero-medial approach, first graft containment arm 110 is disposed in the posterior position, second graft containment arm 115 is disposed in the anterior position, and base 105 is disposed in the antero-medial position, with base 105 extending between and connecting together posterior graft containment arm 110 and anterior graft containment arm 115. In this setting, posterior graft containment arm 110 and anterior graft containment arm 115 are preferably disposed substantially parallel to one another, intersecting the antero-medial base 105 at non-right angles (see FIG. 3), or as otherwise appropriate for the anatomy. Furthermore, in this setting, posterior graft containment arm 110 is longer than anterior graft containment arm 115.

In this form of the invention, base 105, first graft containment arm 110 and second graft containment arm 115 are attached together using a tab and slot interface construction, with the first graft containment arm 110 having a first male (tab) member 120 which is received by a first female (slot) recess 125 formed in base 105, and with the second graft containment arm 115 having a second male (tab) member 130 which is received by a second female (slot) recess 135 formed in base 105. If desired, first male member 120 may form a friction fit in first female recess 125, and/or second male member 130 may form a friction fit in second female recess 135.

If desired, the various components of wedge-shaped implant 100 may be provided with barbs, ridges, projections, roughening, etc., as generally indicated at B (shown in FIG. 4 but omitted from FIG. 3 for the sake of clarity), so as to enhance engagement between the implant components and the bone.

In use, the wedge-shaped implant 100 is positioned in wedge-like opening 25 in tibia 10 so as to stabilize the tibia with the desired geometry while healing occurs. To this end, an appropriately sized base 105, an appropriately sized first graft containment arm 110 and an appropriately sized second graft containment arm 115 are selected from a library of parts, preferably provided to the surgeon in kit form. If desired, the selected parts can be further sized to a desired dimension, e.g., by cutting. In the setting of an antero-medial approach, deployment of implant 100 may be effected by first appropriately positioning posterior graft containment arm 110 and anterior graft containment arm 115 in wedge-like opening 25, and then connecting them together with base 105. As this occurs, posterior graft containment arm 110, anterior graft containment arm 115 and base 105 form a generally U-shaped perimeter which can contain bone paste, bone cement, other bone graft materials or the like within the interior of wedge-like opening 25, whereby to facilitate healing. One or more bone screws 140, installed through openings 145, can be used to screw base 105 to the tibia.

If desired, the first graft containment arm and the second graft containment arm may be joined together by a bridge so as to form a single unit. More particularly, and looking now at FIGS. 5 and 6, there is shown a novel implant 100A which comprises a base 105A, a first graft containment arm 110A, a second graft containment arm 115A, and a bridge 150A connecting together first graft containment arm 110A and second graft containment arm 115A. Again, base 105A, first graft containment arm 110A and second graft containment arm 115A are attached together using a tab and slot interface construction, with the first graft containment arm 110A having a first male (tab) member 120A which is received by a first female (slot) recess 125A formed in base 105A, and with the second graft containment arm 115A having a second male (tab) member 130A which is received by a second female (slot) recess 135A formed in base 105A. If desired, first male member 120A may form a friction fit in first female recess 125A, and/or second male member 130A may form a friction fit in second female recess 135A. Again, a screw 140A, received through an opening 145A in base 105A, may be used to screw base 105A to the tibia. If desired, the various components of wedge-shaped implant 100A may be provided with barbs, ridges, projections, roughening, etc., as generally indicated at B (shown in FIG. 6 but omitted from FIG. 5 for the sake of clarity), so as to enhance engagement between the implant components and the bone.

If desired, the positions of the tabs and slots can be reversed, i.e., with the base having a first male (tab) member which is received in a first female (slot) member formed in the first graft containment arm, and with the base having a second male (tab) member which is received in a second female (slot) member formed in second graft containment arm. More particularly, and looking now at FIGS. 7 and 8, there is shown a novel implant 100B which is substantially the same as implant 100 described above, except that the position of the tabs and slots is reversed; and in FIGS. 9 and 10, there is shown a novel implant 100C which is substantially the same as implant 100A described above, except that the position of the tabs and slots is reversed.

Multi-Part Implant with Wedge and Groove Interface Construction

Figure 11:
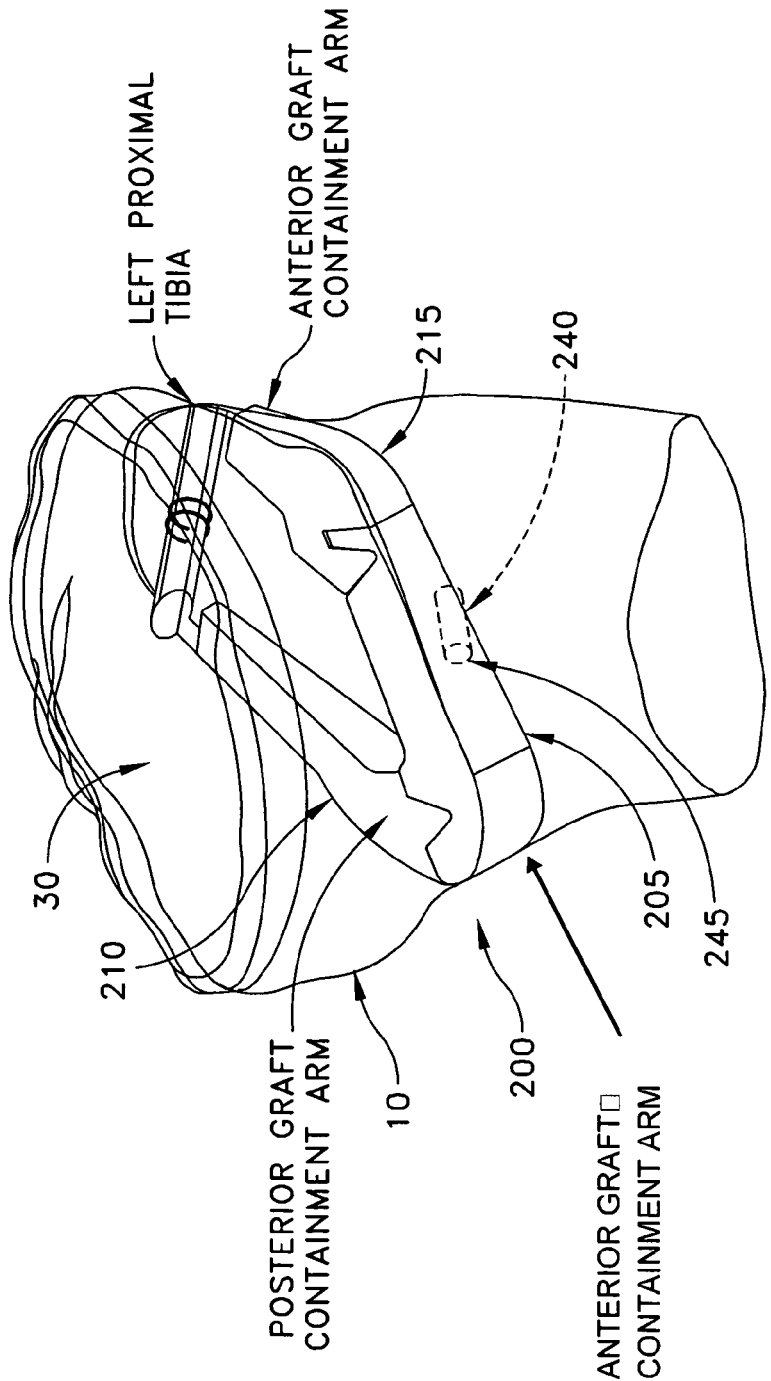
FIGS. 11-18 are schematic views showing various multi-part implants with wedge and groove interface construction.
Figure 12:
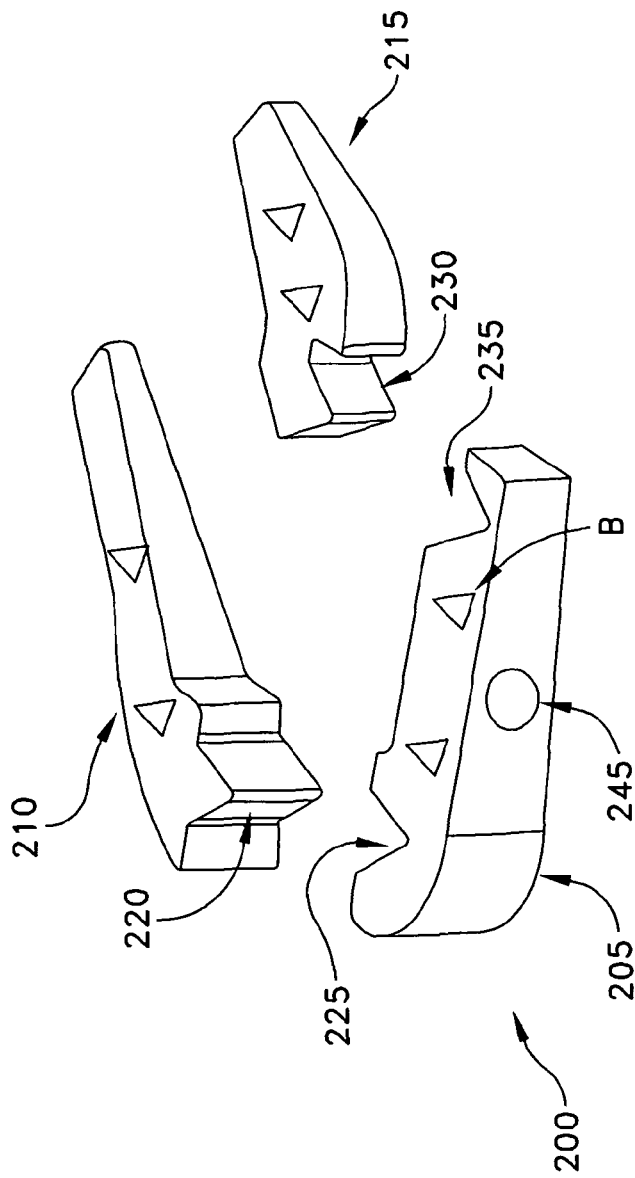

Looking next at FIGS. 11 and 12, in one preferred form of the invention, there is provided a novel implant 200 which generally comprises a base 205, a first graft containment arm 210 and a second graft containment arm 215. Base 205, first graft containment arm 210 and second graft containment arm 215 are intended to be attached together, preferably in-situ, so as to collectively form a generally wedge-shaped structure, with base 205 constituting the thicker end of the wedge. In the case where wedge-shaped opening 25 is formed using an antero-medial approach (e.g., such as that shown in FIG. 11), so that implant 200 is positioned using an antero-medial approach, first graft containment arm 210 is disposed in the posterior position, second graft containment arm 215 is disposed in the anterior position, and base 205 is disposed in the antero-medial position, with base 205 extending between and connecting together posterior graft containment arm 210 and anterior graft containment arm 215. In this setting, posterior graft containment arm 210 and anterior graft containment arm 215 are preferably disposed substantially parallel to one another, intersecting the antero-medial base 205 at non-right angles (see FIG. 11), or as otherwise appropriate for the anatomy. Furthermore, in this setting, posterior graft containment arm 210 is longer than anterior graft containment arm 215.

In this form of the invention, base 205, first graft containment arm 210 and second graft containment arm 215 are attached together using a wedge and groove interface construction, with the first graft containment arm 210 having a first male (wedge) member 220 which is received by a first female (groove) recess 225 formed in base 205, and with the second graft containment arm 215 having a second male (wedge) member 230 which is received by a second female (groove) recess 235 formed in base 205. If desired, first male member 220 may form a friction fit in first female recess 225, and/or second male member 230 may form a friction fit in second female recess 235.

If desired, the various components of wedge-shaped implant 200 may be provided with barbs, ridges, projections, roughening, etc., as generally indicated at B (shown in FIG. 12 but omitted from FIG. 11 for the sake of clarity), so as to enhance engagement between the implant components and the bone.

In use, the wedge-shaped implant 200 is positioned in wedge-like opening 25 in tibia 10 so as to stabilize the tibia with the desired geometry while healing occurs. To this end, an appropriately sized base 205, an appropriately sized first graft containment arm 210 and an appropriately sized second graft containment arm 215 are selected from a library of parts, preferably provided to the surgeon in kit form. If desired, the selected parts can be further sized to a desired dimension, e.g., by cutting. In the setting of an antero-medial approach, deployment of implant 200 may be effected by first appropriately positioning posterior graft containment arm 210 and anterior graft containment arm 215 in wedge-like opening 25, and then connecting them together with base 205. As this occurs, posterior graft containment arm 210, anterior graft containment arm 215 and base 205 form a generally U-shaped perimeter which can contain bone paste, bone cement, other bone graft materials or the like within the interior of wedge-like opening 25, whereby to facilitate healing. One or more bone screws 240, installed through openings 245, can be used to screw base 205 to the tibia.

If desired, the first graft containment arm and the second graft containment arm may be joined together by a bridge so as to form a single unit. More particularly, and looking now at FIGS. 13 and 14, there is shown a novel implant 200A which comprises a base 205A, a first graft containment arm 210A, a second graft containment arm 215A, and a bridge 250A connecting together first graft containment arm 210A and second graft containment arm 215A. Again, base 205A, first graft containment arm 210A and second graft containment arm 215A are attached together using a wedge and groove interface construction, with the first graft containment arm 210A having a first male (wedge) member 220A which is received by a first female (groove) recess 225A formed in base 205A, and with the second graft containment arm 215A having a second male (wedge) member 230A which is received by a second female (groove) recess 235A formed in base 205A. If desired, first male member 220A may form a friction fit in first female recess 225A, and/or second male member 230A may form a friction fit in second female recess 235A. Again, a screw 240A, received through an opening 245A in base 205A, may be used to screw base 205A to the tibia. If desired, the various components of wedge-shaped implant 200A may be provided with barbs, ridges, projections, roughening, etc., as generally indicated at B (shown in FIG. 14 but omitted from FIG. 13 for the sake of clarity), so as to enhance engagement between the implant components and the bone.

If desired, the positions of the wedges and grooves can be reversed, i.e., with the base having a first male (wedge) member which is received in a first female (groove) member formed in the first graft containment arm, and with the base having a second male (wedge) member which is received in a second female (groove) member formed in second graft containment arm. More particularly, and looking now at FIGS. 15 and 16, there is shown a novel implant 200B which is substantially the same as implant 200 described above, except that the position of the wedges and grooves is reversed; and in FIGS. 17 and 18, there is shown a novel implant 200C which is substantially the same as implant 200A described above, except that the position of the wedges and grooves is reversed.

Multi-Part Implant with Ball and Socket Interface Construction

Figure 19:
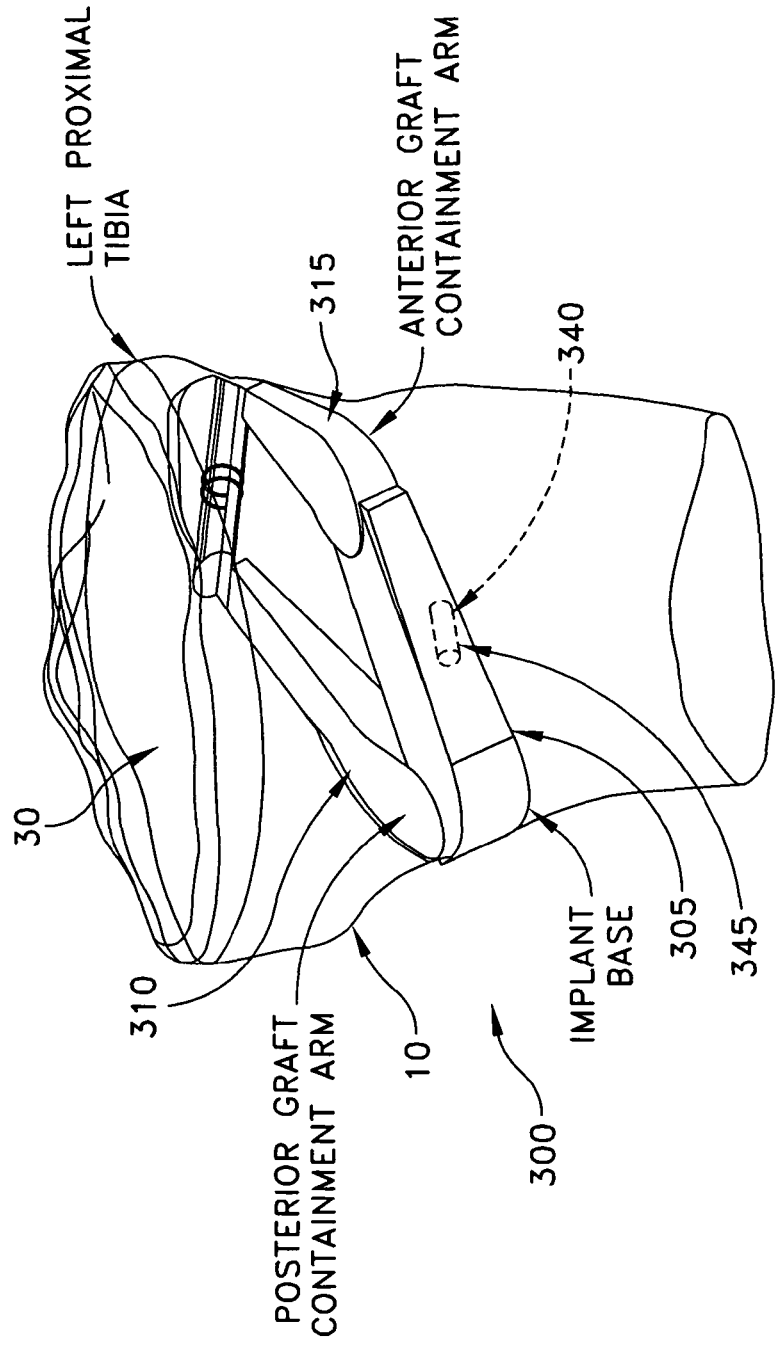
FIGS. 19-26 are schematic views showing various multi-part implants with ball and socket interface construction.
Figure 20:
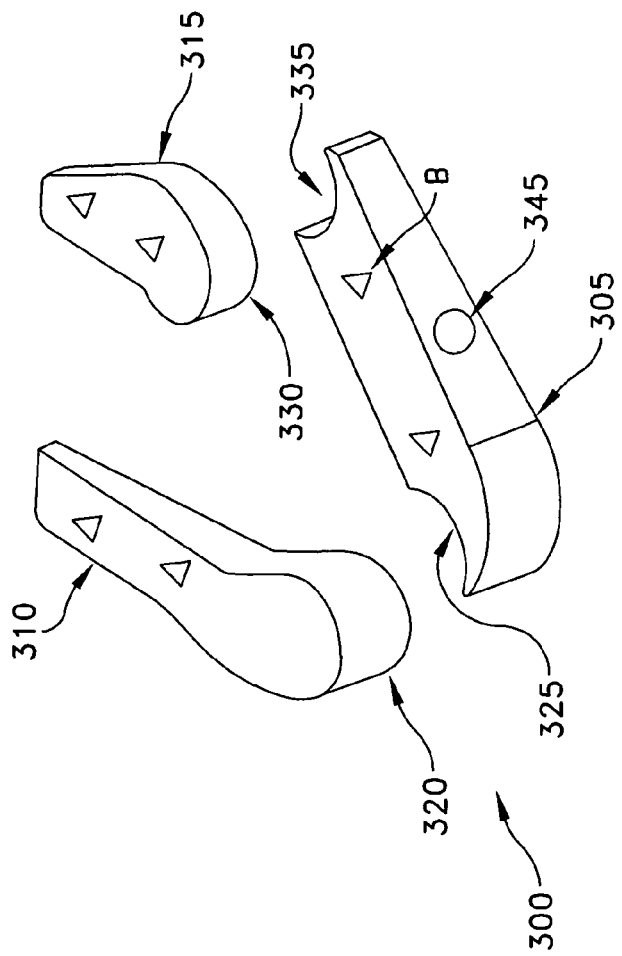

Looking next at FIGS. 19 and 20, in one preferred form of the invention, there is provided a novel implant 300 which generally comprises a base 305, a first graft containment arm 310 and a second graft containment arm 315. Base 305, first graft containment arm 310 and second graft containment arm 315 are intended to be attached together, preferably in-situ, so as to collectively form a generally wedge-shaped structure, with base 305 constituting the thicker end of the wedge. In the case where wedge-shaped opening 25 is formed using an antero-medial approach (e.g., such as that shown in FIG. 19), so that implant 300 is positioned using an antero-medial approach, first graft containment arm 310 is disposed in the posterior position, second graft containment arm 315 is disposed in the anterior position, and base 305 is disposed in the antero-medial position, with base 305 extending between and connecting together posterior graft containment arm 310 and anterior graft containment arm 315. In this setting, posterior graft containment arm 310 and anterior graft containment arm 315 are preferably disposed substantially parallel to one another, intersecting the antero-medial base 305 at non-right angles (see FIG. 19), or as otherwise appropriate for the anatomy. Furthermore, in this setting, posterior graft containment arm 310 is longer than anterior graft containment arm 315.

In this form of the invention, base 305, first graft containment arm 310 and second graft containment arm 315 are attached together using a ball and socket interface construction, with the first graft containment arm 310 having a first male (ball) member 320 which is received by a first female (socket) recess 325 formed in base 305, and with the second graft containment arm 315 having a second male (ball) member 330 which is received by a second female (socket) recess 335 formed in base 305. If desired, first male member 320 may form a friction fit in first female recess 325, and/or second male member 330 may form a friction fit in second female recess 335.

Significantly, the use of a ball and socket interface construction permits in-situ adjustment of the joinder angle between first graft containment arm 310 and base 305, and in-situ adjustment of the joinder angle between second graft containment arm 315 and base 305. This provides flexibility for addressing patient-specific variations in anatomy, and can significantly reduce inventory requirements.

If desired, the various components of wedge-shaped implant 300 may be provided with barbs, ridges, projections, roughening, etc., as generally indicated at B (shown in FIG. 20 but omitted from FIG. 19 for the sake of clarity), so as to enhance engagement between the implant components and the bone.

In use, the wedge-shaped implant 300 is positioned in wedge-like opening 25 in tibia 10 so as to stabilize the tibia with the desired geometry while healing occurs. To this end, an appropriately sized base 305, an appropriately sized first graft containment arm 310 and an appropriately sized second graft containment arm 315 are selected from a library of parts, preferably provided to the surgeon in kit form. If desired, the selected parts can be further sized to a desired dimension, e.g., by cutting. In the setting of an antero-medial approach, deployment of implant 300 may be effected by first appropriately positioning posterior graft containment arm 310 and anterior graft containment arm 315 in wedge-like opening 25, and then connecting them together with base 305. As this occurs, posterior graft containment arm 310, anterior graft containment arm 315 and base 305 form a generally U-shaped perimeter which can contain bone paste, bone cement, other bone graft materials or the like within the interior of wedge-like opening 25, whereby to facilitate healing. One or more bone screws 340, installed through openings 345, can be used to screw base 305 to the tibia.

Again, the use of a ball and socket interface construction permits in-situ adjustment of the joinder angles between (i) first graft containment arm 310 and base 305, and (ii) second graft containment arm 315 and base 305. This provides flexibility for addressing patient-specific variations in anatomy, and can significantly reduce inventory requirements.

Figure 21:
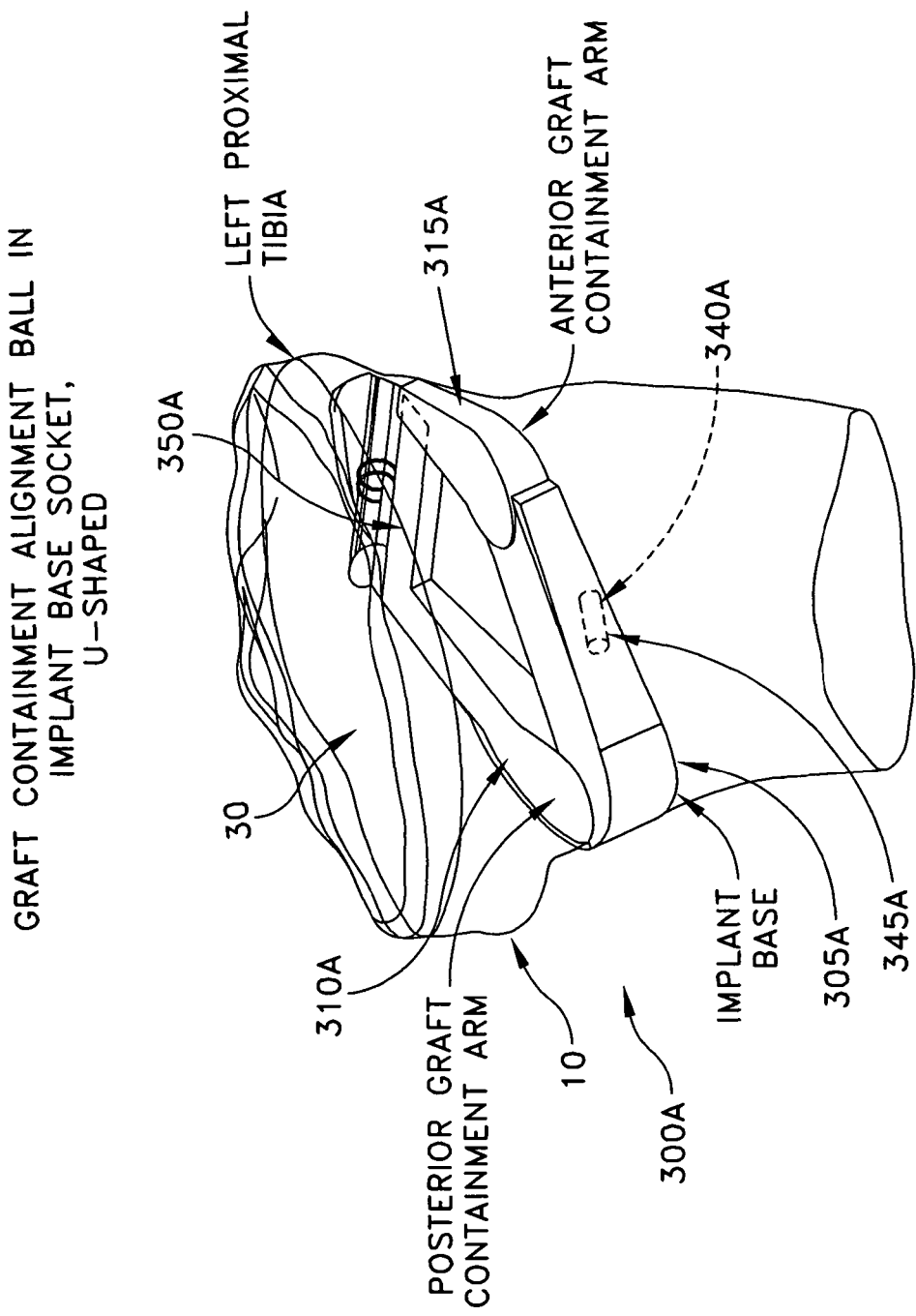
Figure 22:
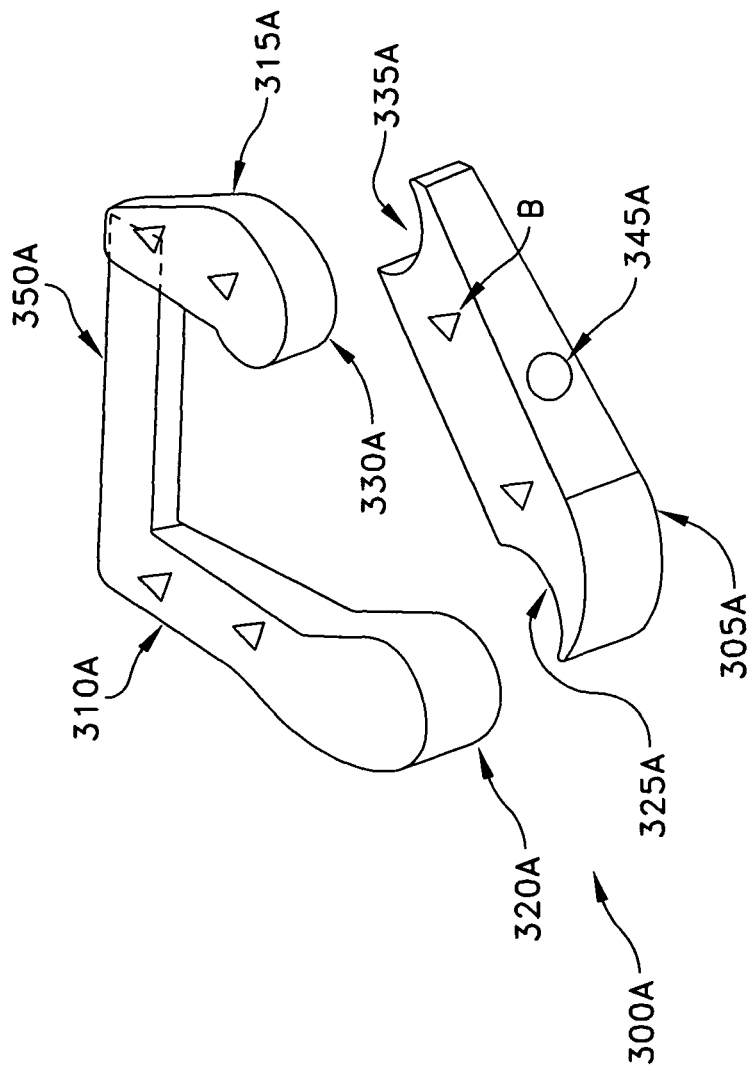

If desired, the first graft containment arm and the second graft containment arm may be joined together by a bridge so as to form a single unit. More particularly, and looking now at FIGS. 21 and 22, there is shown a novel implant 300A which comprises a base 305A, a first graft containment arm 310A, a second graft containment arm 315A, and a bridge 350A connecting together first graft containment arm 310A and second graft containment arm 315A. Again, base 305A, first graft containment arm 310A and second graft containment arm 315A are attached together using a ball and socket interface construction, with the first graft containment arm 310A having a first male (ball) member 320A which is received by a first female (socket) recess 325A formed in base 305A, and with the second graft containment arm 315A having a second male (ball) member 330A which is received by a second female (socket) recess 335A formed in base 305A. If desired, first male member 320A may form a friction fit in first female recess 325A, and/or second male member 330A may form a friction fit in second female recess 335A. Again, a screw 340A, received through an opening 345A in base 305A, may be used to screw base 305A to the tibia. If desired, the various components of wedge-shaped implant 300A may be provided with barbs, ridges, projections, roughening, etc., as generally indicated at B (shown in FIG. 22 but omitted from FIG. 21 for the sake of clarity), so as to enhance engagement between the implant components and the bone.

Figure 23:
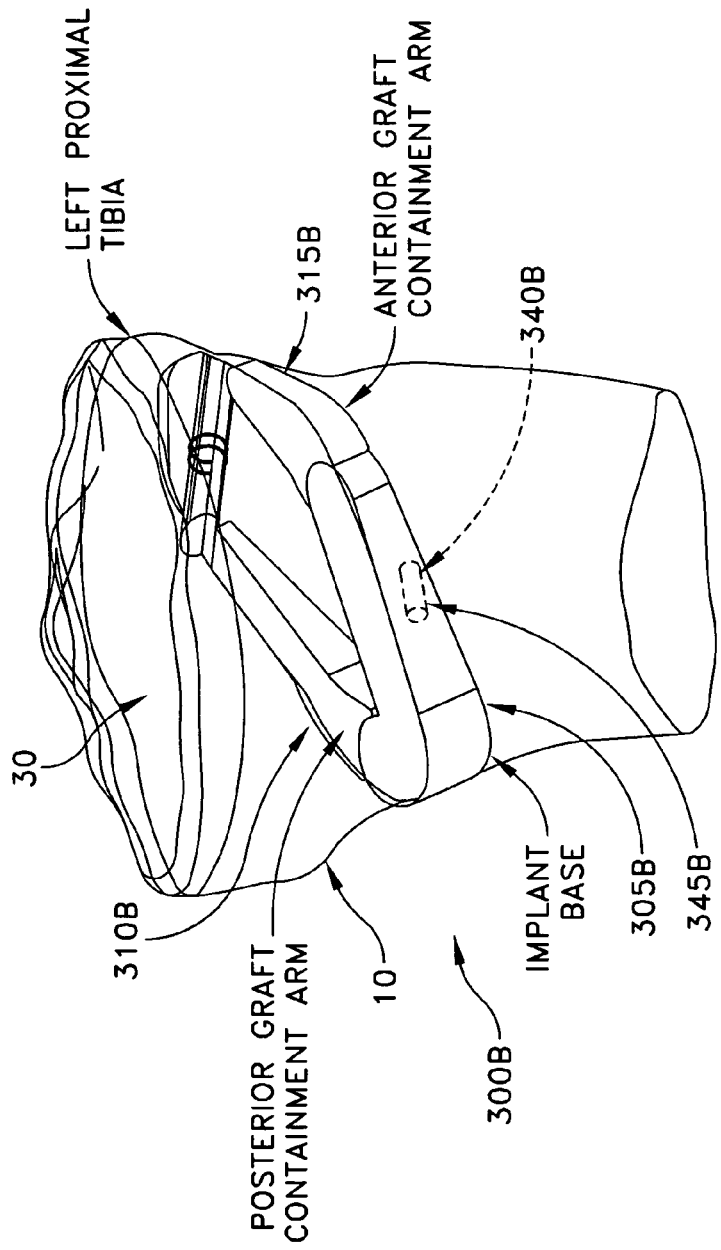
Figure 24:
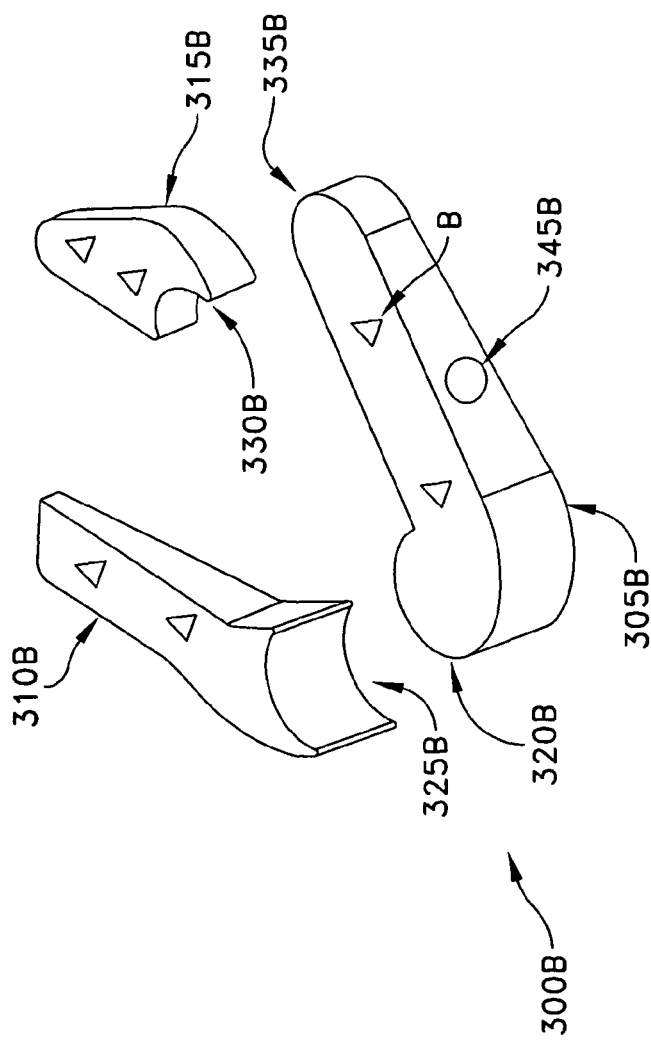
Figure 25:
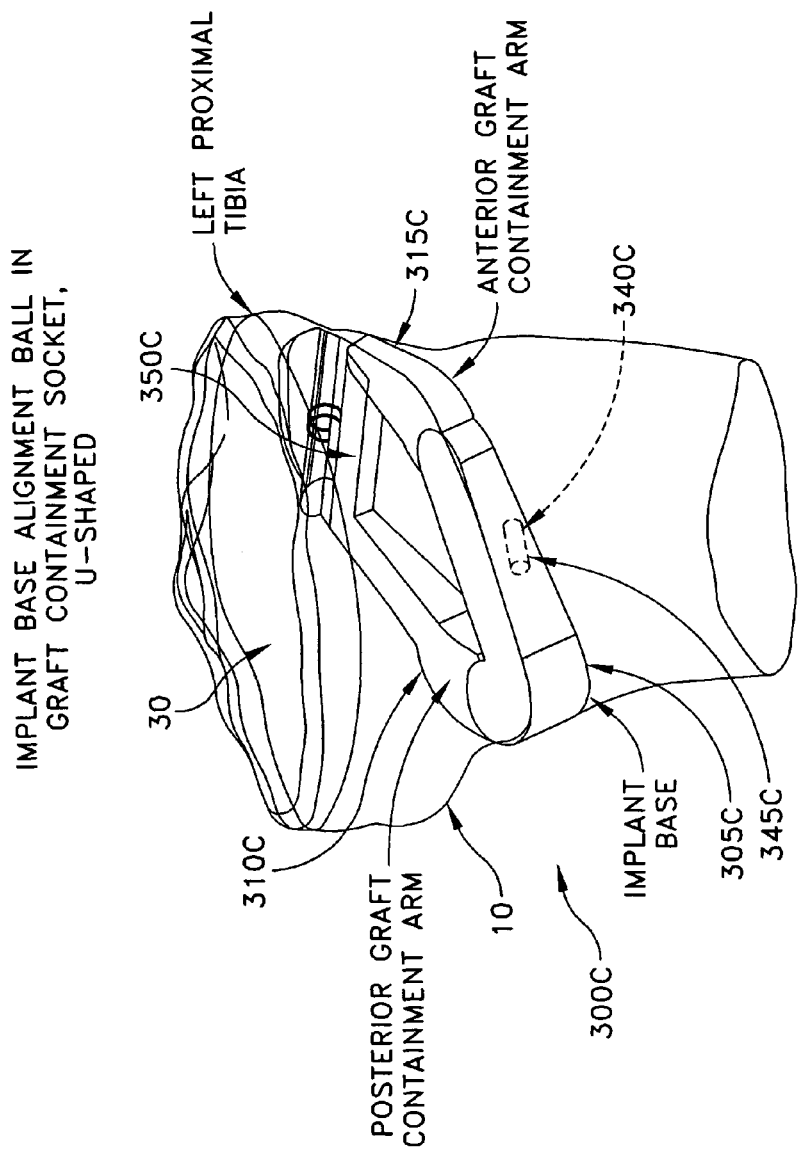
Figure 26:
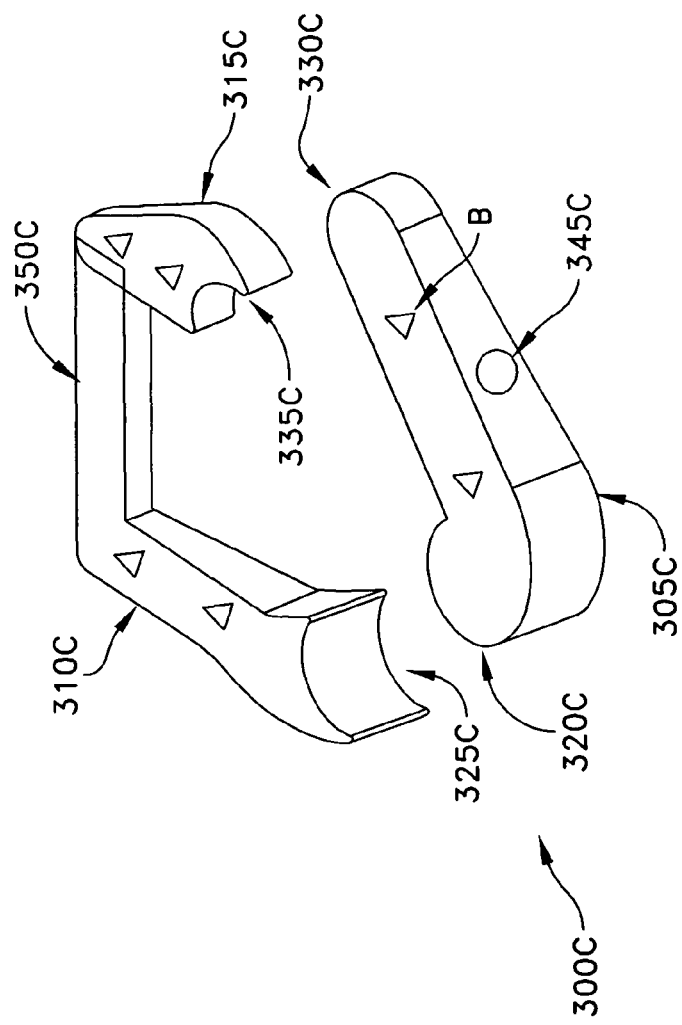

If desired, the positions of the balls and sockets can be reversed, i.e., with the base having a first male (ball) member which is received in a first female (socket) member formed in the first graft containment arm, and with the base having a second male (ball) member which is received in a second female (socket) member formed in second graft containment arm. More particularly, and looking now at FIGS. 23 and 24, there is shown a novel implant 300B which is substantially the same as implant 300 described above, except that the position of the balls and sockets is reversed; and in FIGS. 25 and 26, there is shown a novel implant 300C which is substantially the same as implant 300A described above, except that the position of the balls and sockets is reversed.

Multi-Part Implant with Flat-To-Flat Interface Construction

Figure 27:
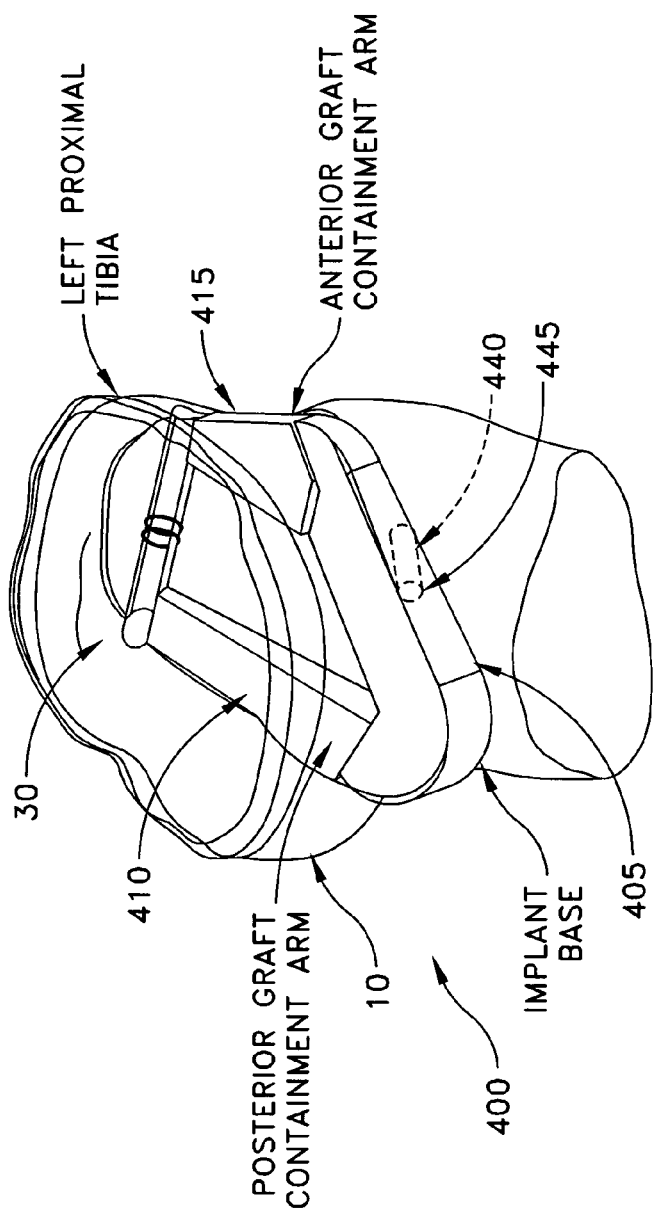
FIGS. 27-34 are schematic views showing various multi-part implants with flat-to-flat interface construction.
Figure 28:
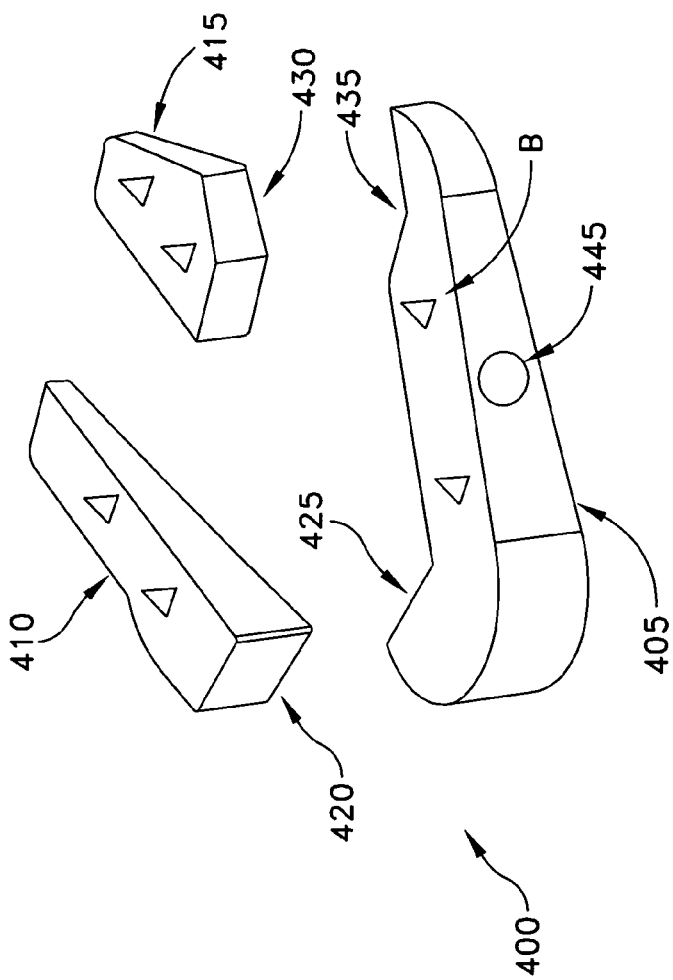

Looking next at FIGS. 27 and 28, in one preferred form of the invention, there is provided a novel implant 400 which generally comprises a base 405, a first graft containment arm 410 and a second graft containment arm 415. Base 405, first graft containment arm 410 and second graft containment arm 415 are intended to be attached together, preferably in-situ, so as to collectively form a generally wedge-shaped structure, with base 405 constituting the thicker end of the wedge. In the case where wedge-shaped opening 25 is formed using an antero-medial approach (e.g., such as that shown in FIG. 27), so that implant 400 is positioned using an antero-medial approach, first graft containment arm 410 is disposed in the posterior position, second graft containment arm 415 is disposed in the anterior position, and base 405 is disposed in the antero-medial position, with base 405 extending between and connecting together posterior graft containment arm 410 and anterior graft containment arm 415. In this setting, posterior graft containment arm 410 and anterior graft containment arm 415 are preferably disposed substantially parallel to one another, intersecting the antero-medial base 405 at non-right angles (see FIG. 27), or as otherwise appropriate for the anatomy. Furthermore, in this setting, posterior graft containment arm 410 is longer than anterior graft containment arm 415.

In this form of the invention, base 405, first graft containment arm 410 and second graft containment arm 415 are attached together using a flat-to-flat interface construction, with the first graft containment arm 410 having a first flat surface 420 which engages a first flat surface 425 formed in base 405, and with the second graft containment arm 415 having a second flat surface 430 which engages a second flat surface 435 formed in base 405. In one preferred construction (see FIGS. 27 and 28), first flat surface 420 and second flat surface 430 are arranged so as to be outwardly facing, in the sense that they project away from the interior of the implant;

and first flat surface 425 and second flat surface 435 are arranged so as to be inwardly facing, in the sense that they project toward the interior of the implant.

If desired, the various components of wedge-shaped implant 400 may be provided with barbs, ridges, projections, roughening, etc., as generally indicated at B (shown in FIG. 28 but omitted from FIG. 27 for the sake of clarity), so as to enhance engagement between the implant components and the bone.

In use, the wedge-shaped implant 400 is positioned in wedge-like opening 25 in tibia 10 so as to stabilize the tibia with the desired geometry while healing occurs. To this end, an appropriately sized base 405, an appropriately sized first graft containment arm 410 and an appropriately sized second graft containment arm 415 are selected from a library of parts, preferably provided to the surgeon in kit form. If desired, the selected parts can be further sized to a desired dimension, e.g., by cutting. In the setting of an antero-medial approach, deployment of implant 400 may be effected by first appropriately positioning posterior graft containment arm 410 and anterior graft containment arm 415 in wedge-like opening 25, and then connecting them together with base 405. As this occurs, posterior graft containment arm 410, anterior graft containment arm 415 and base 405 form a generally U-shaped perimeter which can contain bone paste, bone cement, other bone graft materials or the like within the interior of wedge-like opening 25, whereby to facilitate healing. One or more bone screws 440, installed through openings 445, can be used to screw base 405 to the tibia.

Figure 29:
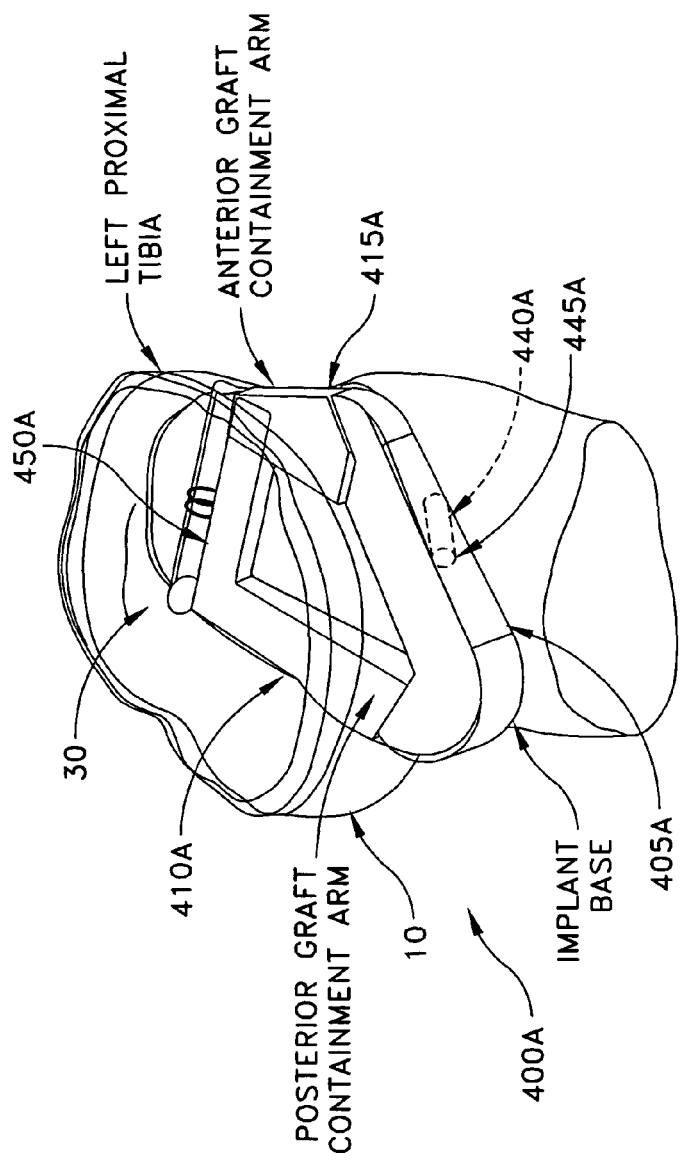
Figure 30:
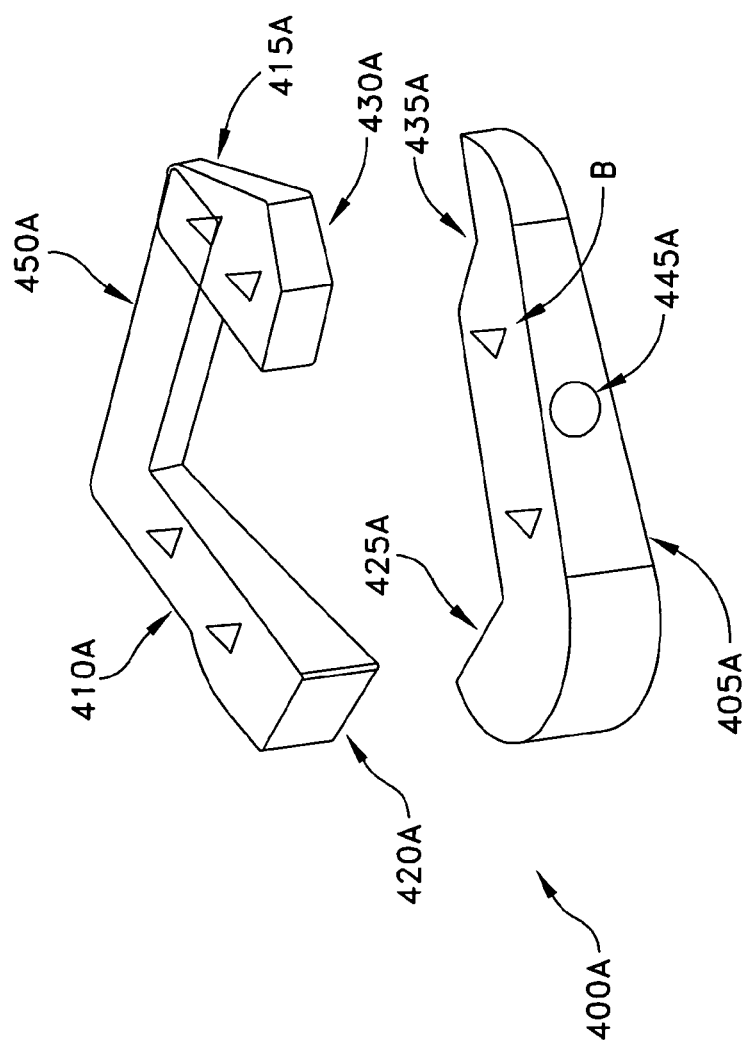

If desired, the first graft containment arm and the second graft containment arm may be joined together by a bridge so as to form a single unit. More particularly, and looking now at FIGS. 29 and 30, there is shown a novel implant 400A which comprises a base 405A, a first graft containment arm 410A, a second graft containment arm 415A, and a bridge 450A connecting together first graft containment arm 410A and second graft containment arm 415A. In one preferred construction (see FIGS. 29 and 30), first flat surface 420A and second flat surface 430A are arranged so as to be outwardly facing, in the sense that they project away from the interior of the implant; and first flat surface 425A and second flat surface 435A are arranged so as to be inwardly facing, in the sense that they project toward the interior of the implant. Again, base 405A, first graft containment arm 410A and second graft containment arm 415A are attached together using a flat-to-flat interface construction, with the first graft containment arm 410A having a first flat surface 420A which engages a first flat surface 425A formed in base 405A, and with the second graft containment arm 415A having a second flat surface 430A which engages a second flat surface 435A formed in base 405A. Again, a screw 440A, received through an opening 445A in base 405A, may be used to screw base 405A to the tibia. If desired, the various components of wedge-shaped implant 400A may be provided with barbs, ridges, projections, roughening, etc., as generally indicated at B (shown in FIG. 30 but omitted from FIG. 29 for the sake of clarity), so as to enhance engagement between the implant components and the bone.

Figure 31:
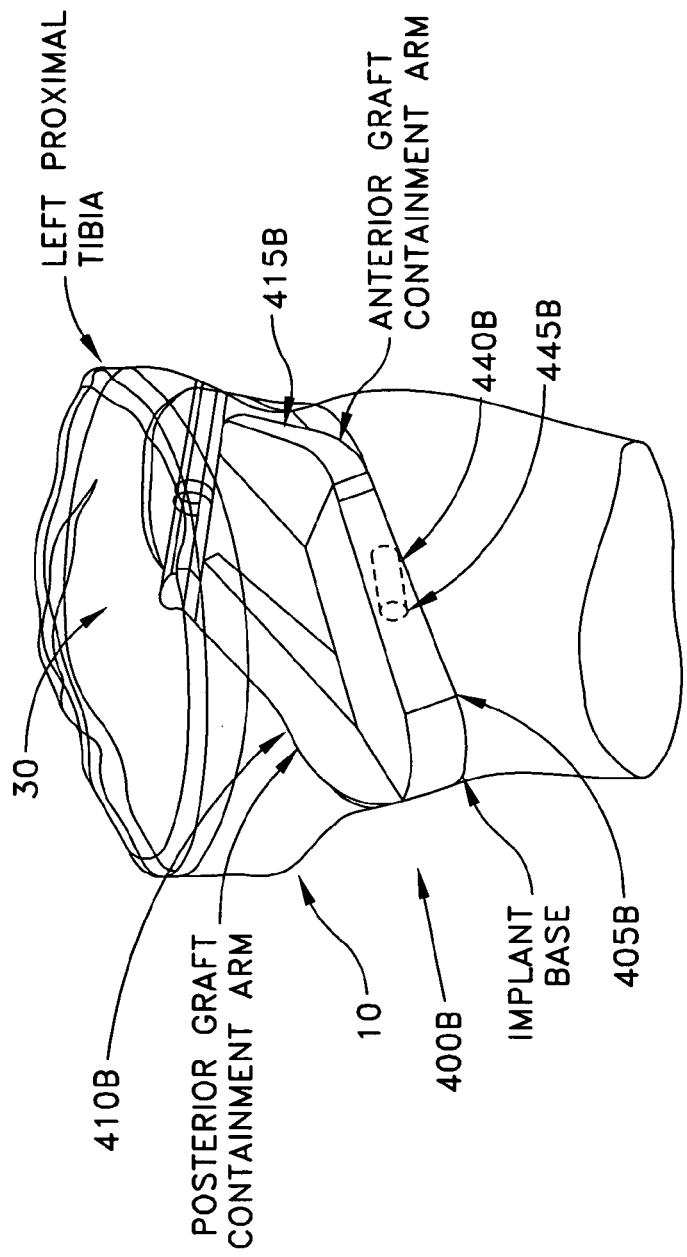
Figure 32:
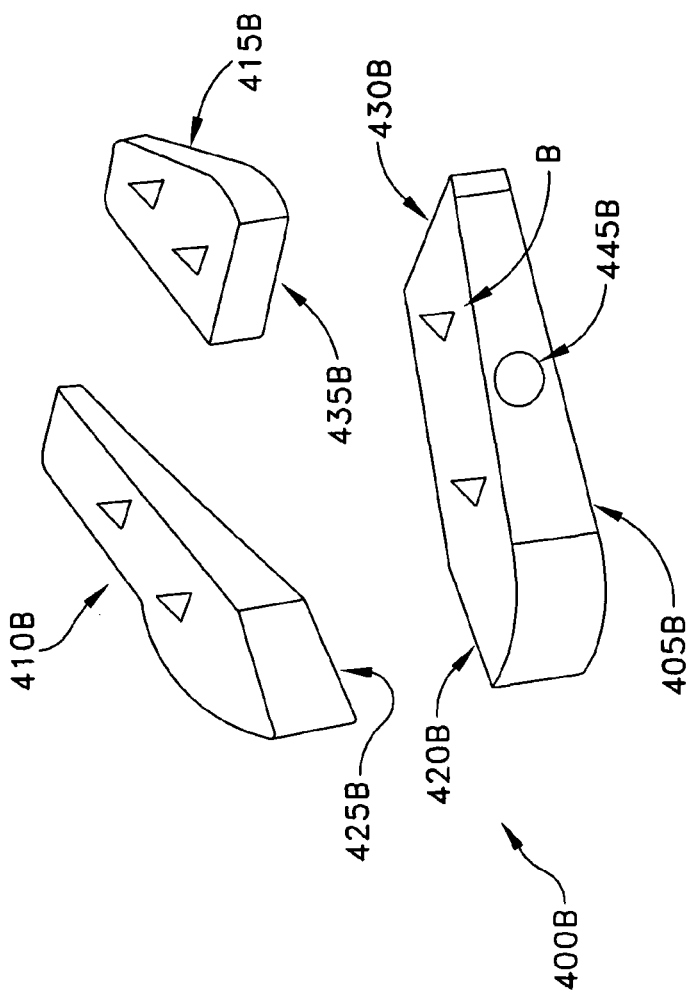
Figure 33:
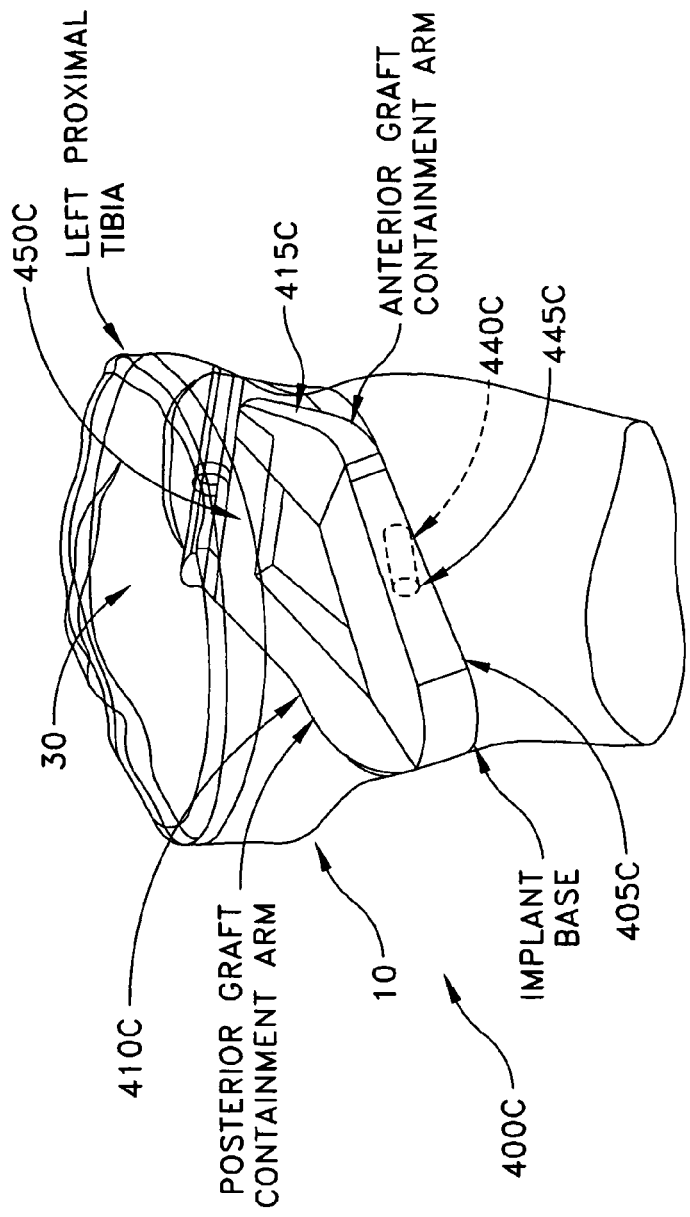
Figure 34:
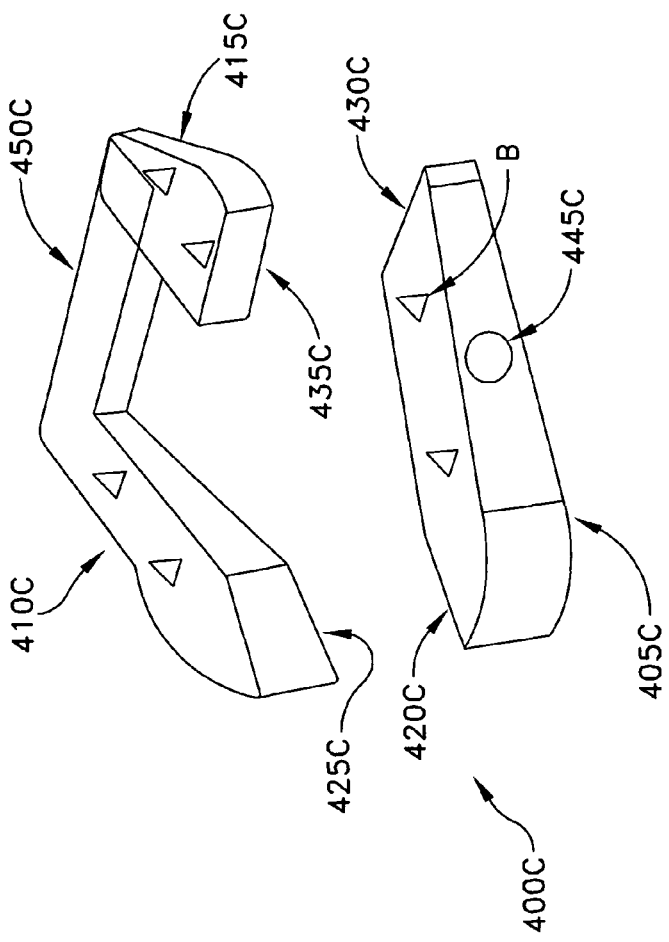

If desired, the positions of the flat surfaces can be reversed. More particularly, and looking now at FIGS. 31 and 32, there is shown a novel implant 400B which is substantially the same as implant 400 described above, except that the positions of the flat surfaces is reversed (i.e., first flat surface 420B and second flat surface 430B are formed on base 405B; and first flat surface 425B and second flat surface 435B are formed on posterior graft containment arm 410B and anterior graft containment arm 415B, respectively); and in FIGS. 33 and 34, there is shown a novel implant 400C which is substantially the same as implant 400A described above, except that the positions of the flat surfaces is reversed (i.e., first flat surface 420C and second flat surface 430C are formed on base 405C; and first flat surface 425C and second flat surface 435C are formed on posterior graft containment arm 410C and anterior graft containment arm 415C, respectively).

OTHER CONFIGURATIONS

In addition to the foregoing, it should also be appreciated that, within a given construct, one graft containment arm might have a male connector (e.g., tab, wedge, ball, etc.) and the other graft containment arm might have a female connector (e.g., slot, groove, socket, etc.).

It should be also appreciated that the various interface constructions disclosed above may be modified by providing multiple engaging elements.

Figure 5:
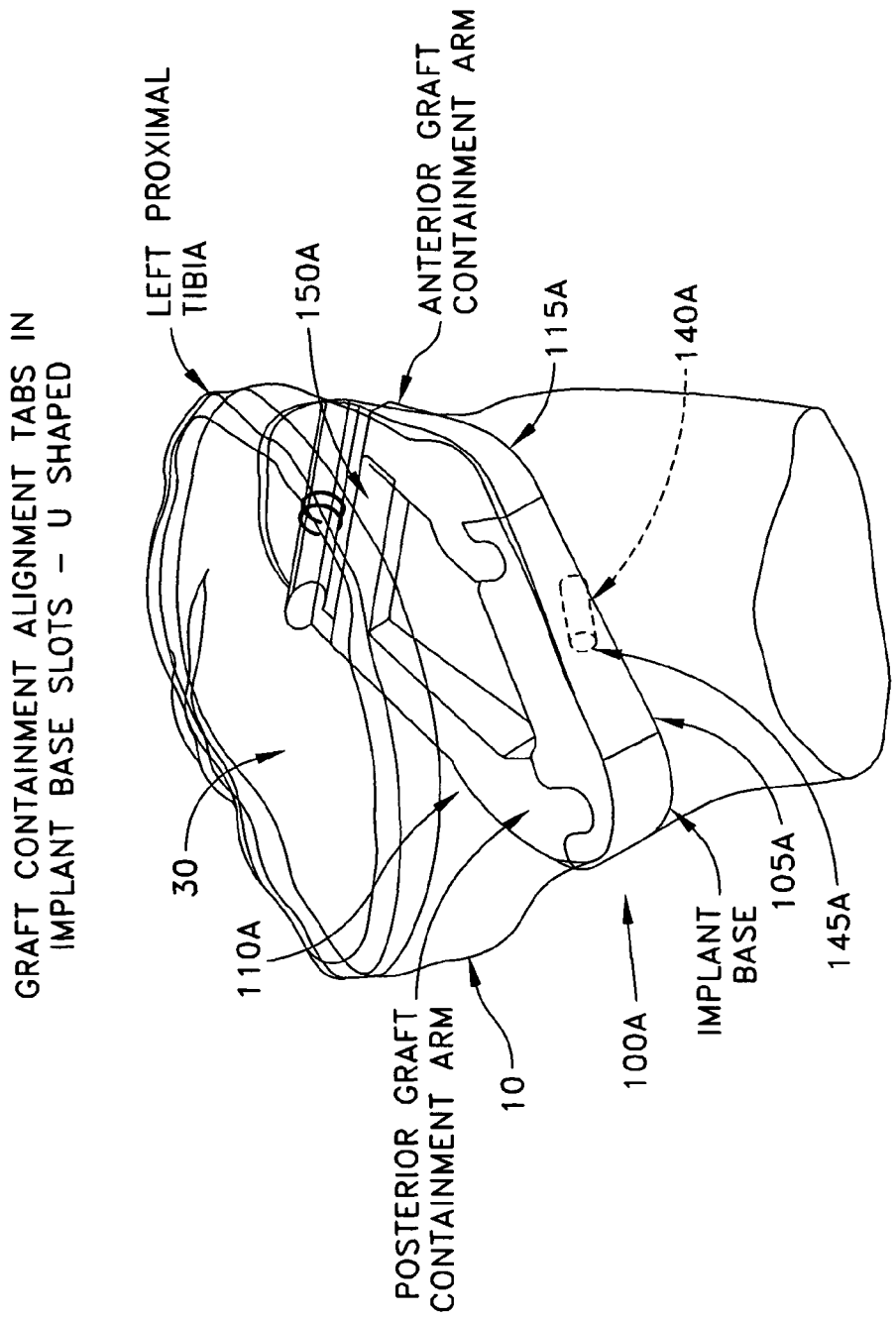
Figure 6:
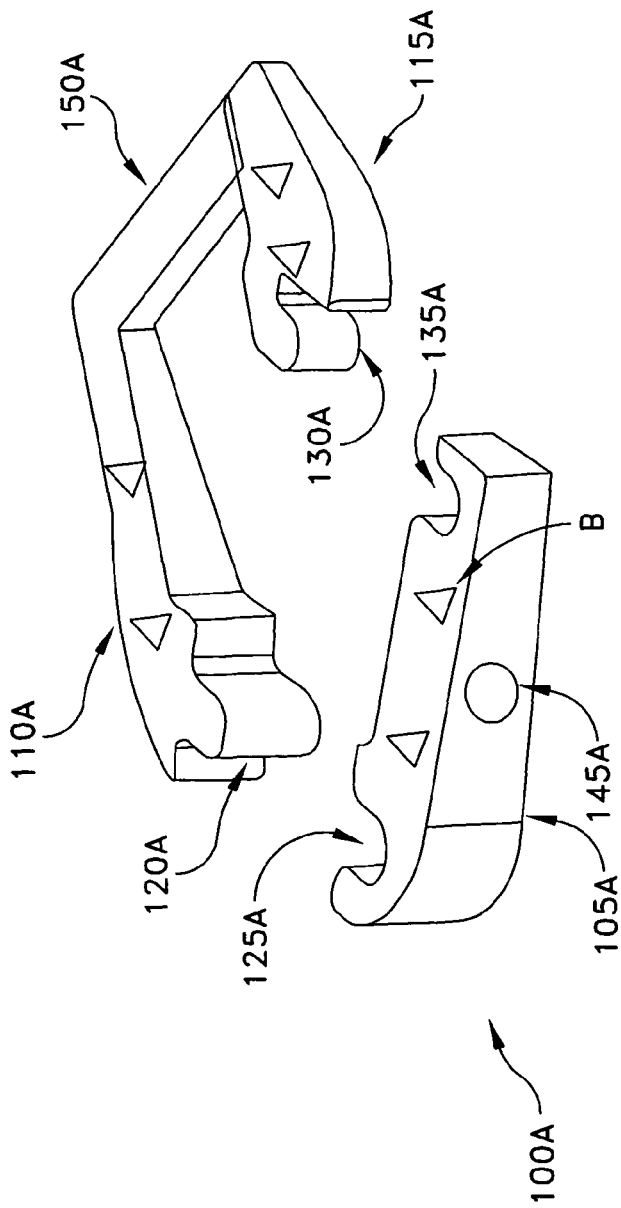
Figure 7:
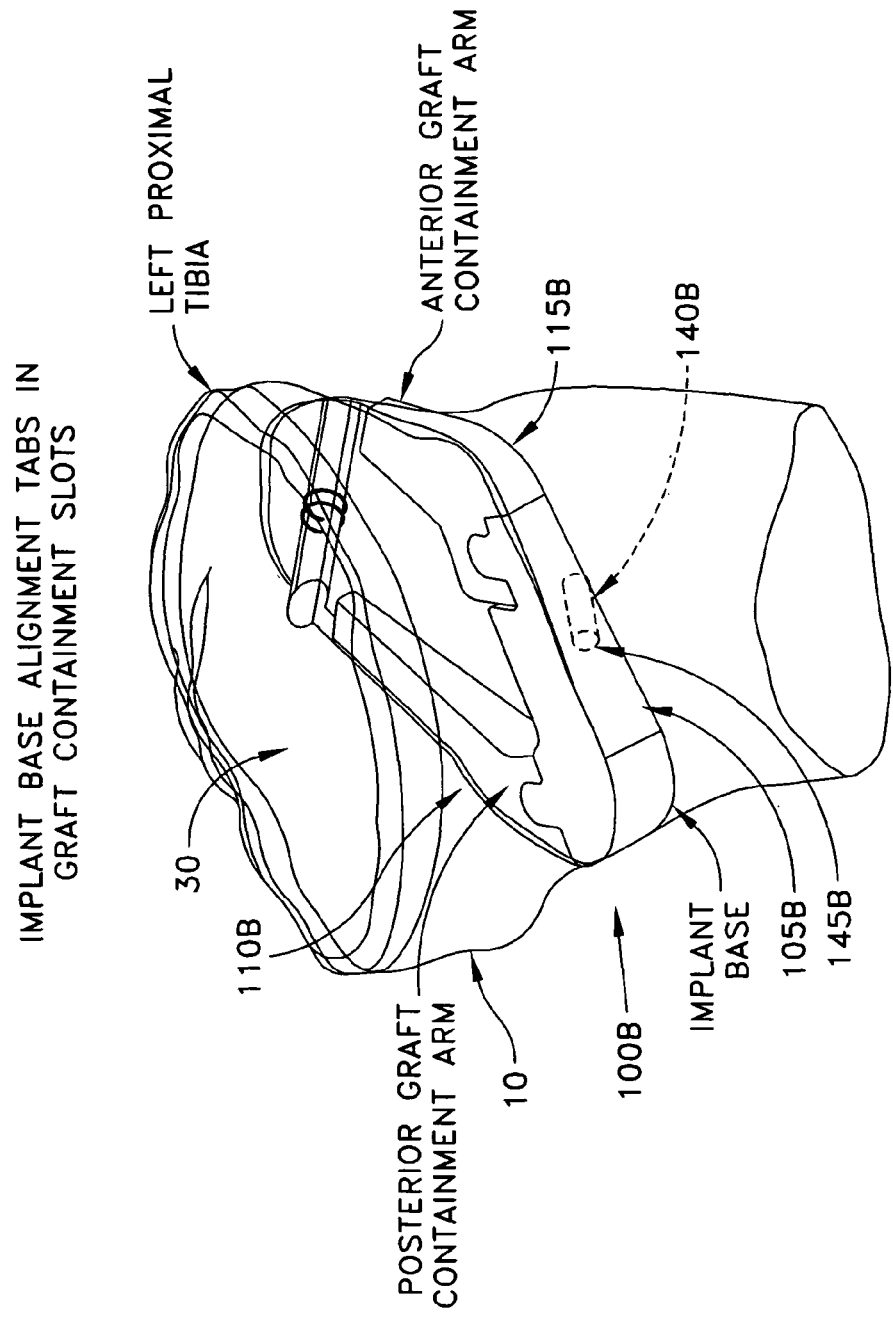
Figure 8:
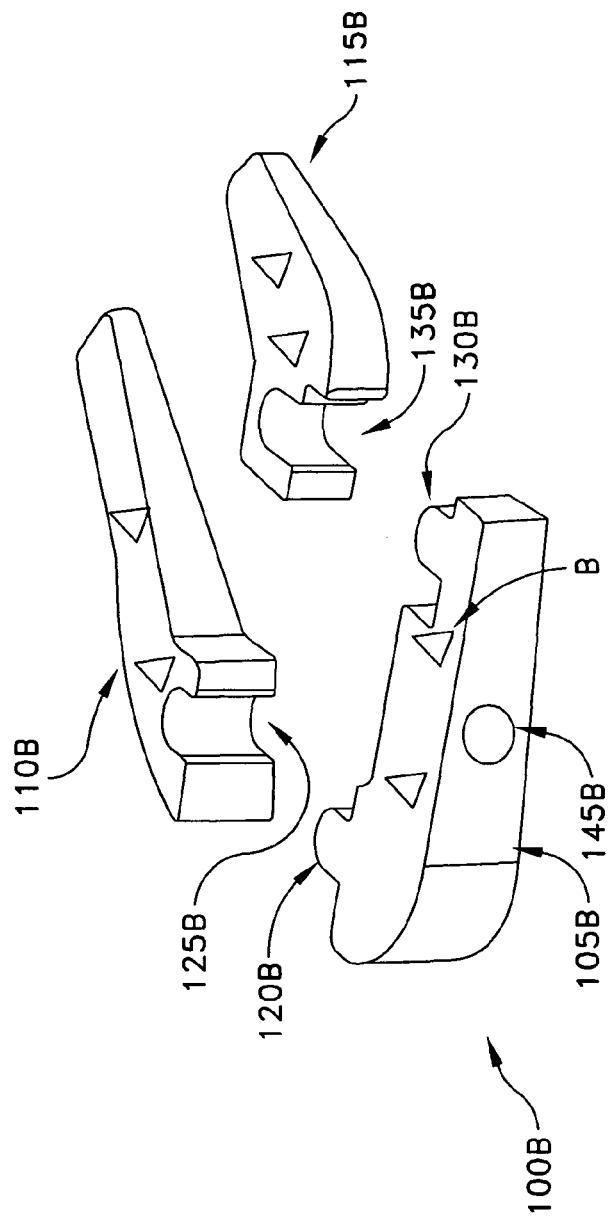
Figure 9:
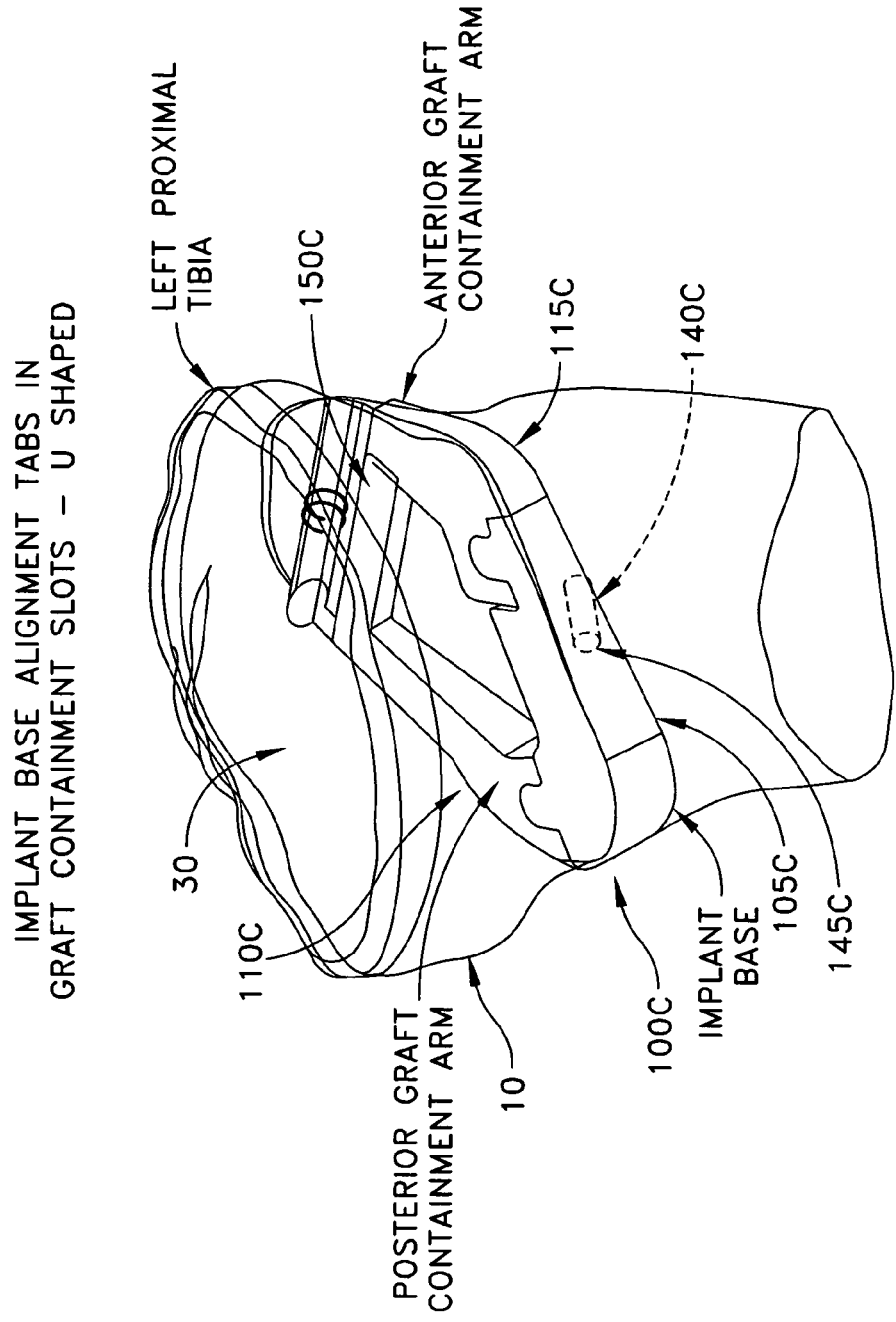
Figure 10:
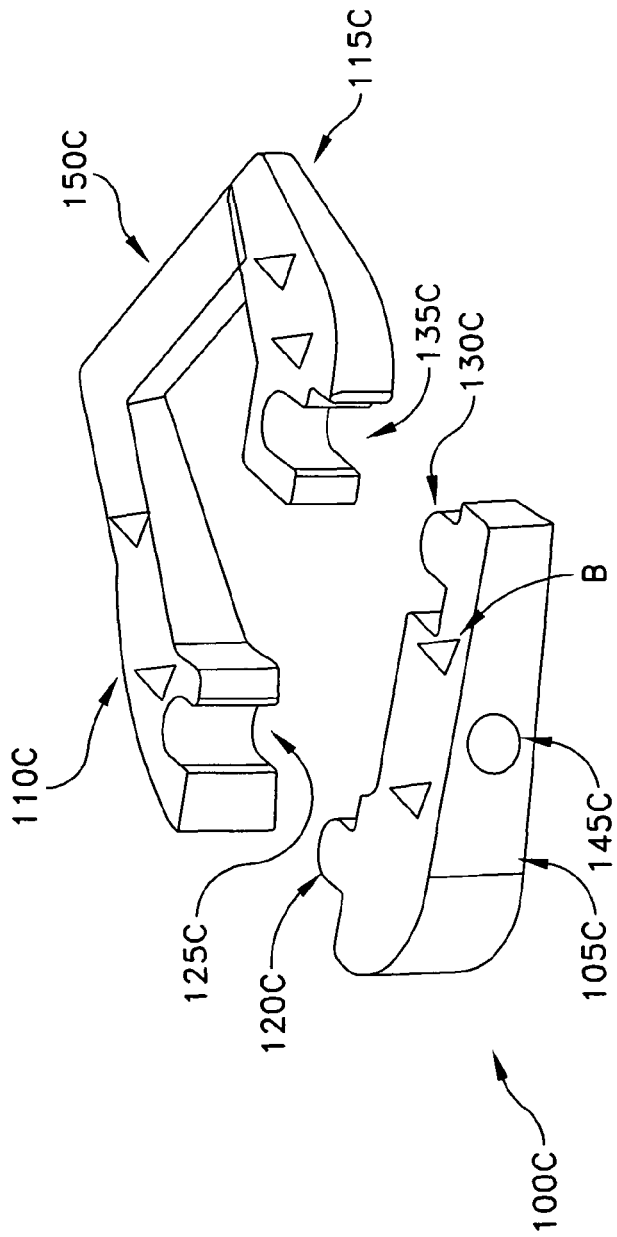

Thus, with the novel implant 100 shown in FIGS. 3 and 4, first graft containment arm 110 and second graft containment arm 115 could each be provided with multiple tabs, etc.; with novel implant 100A shown in FIGS. 5 and 6, first graft containment arm 110A and second graft containment arm 115A could each be provided with multiple tabs, etc.; with novel implant 100B shown in FIGS. 7 and 8, first graft containment arm 110B and second graft containment arm 115B could each be provided with multiple slots, etc.; with the novel implant 100C shown in FIGS. 9 and 10, first graft containment arm 110C and second graft containment arm 115C could each be provided with multiple slots, etc.

Figure 13:
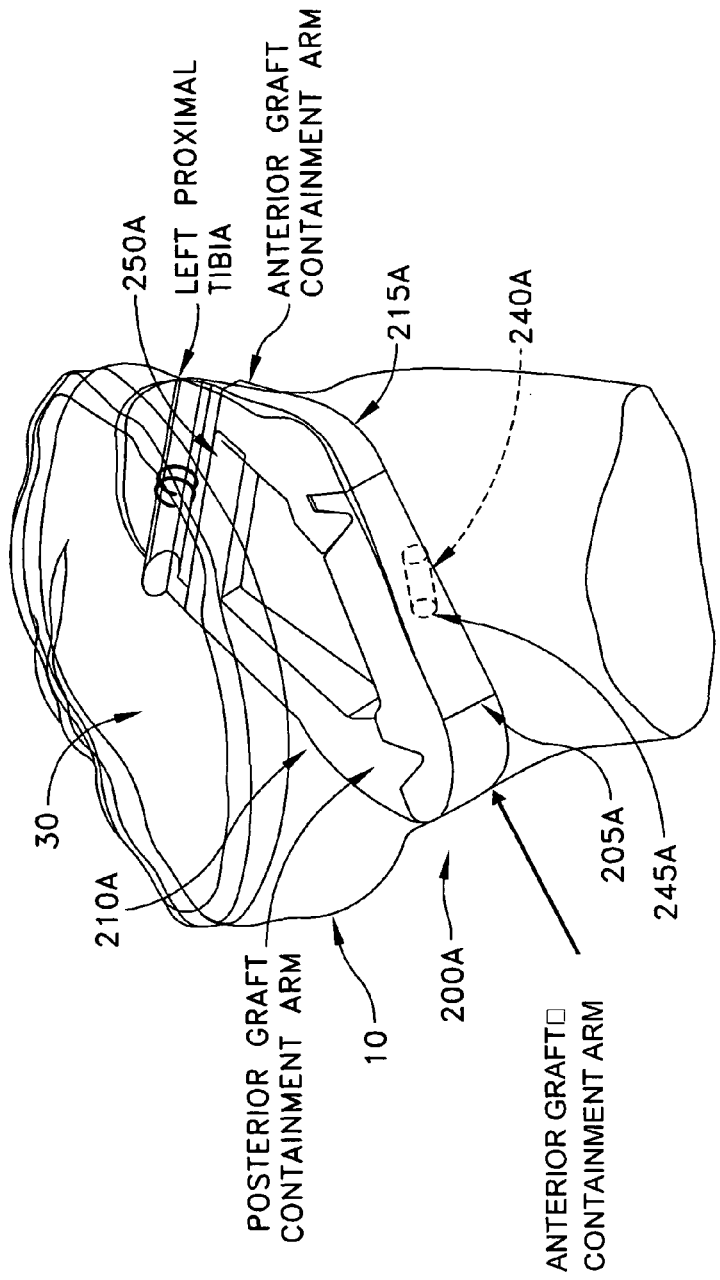
Figure 14:
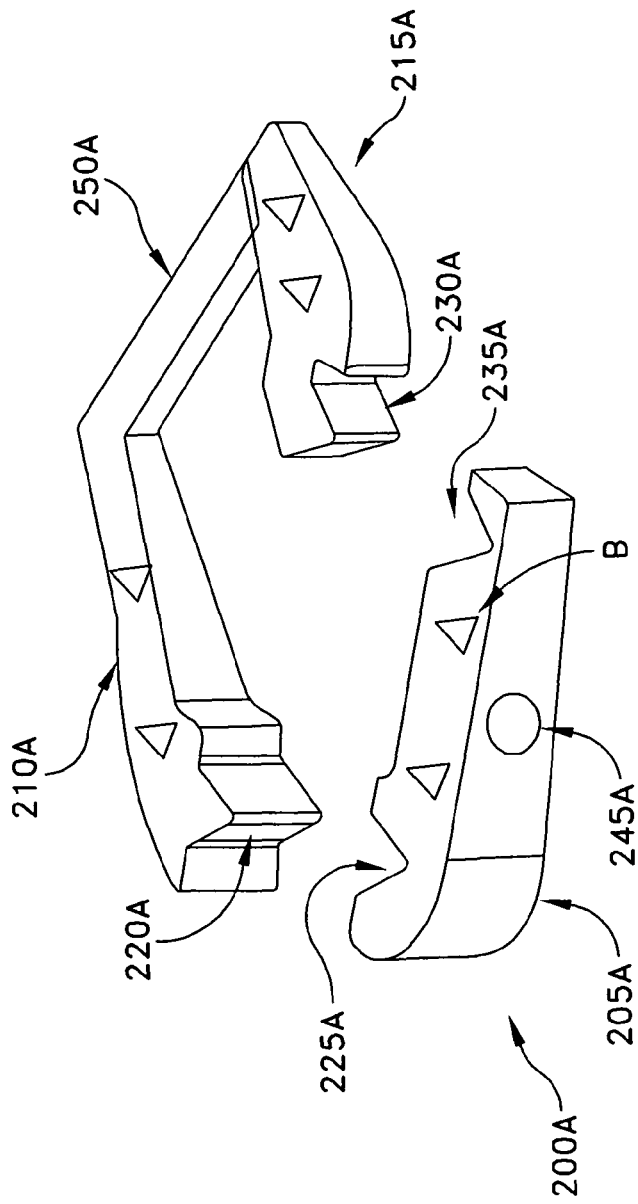
Figure 15:
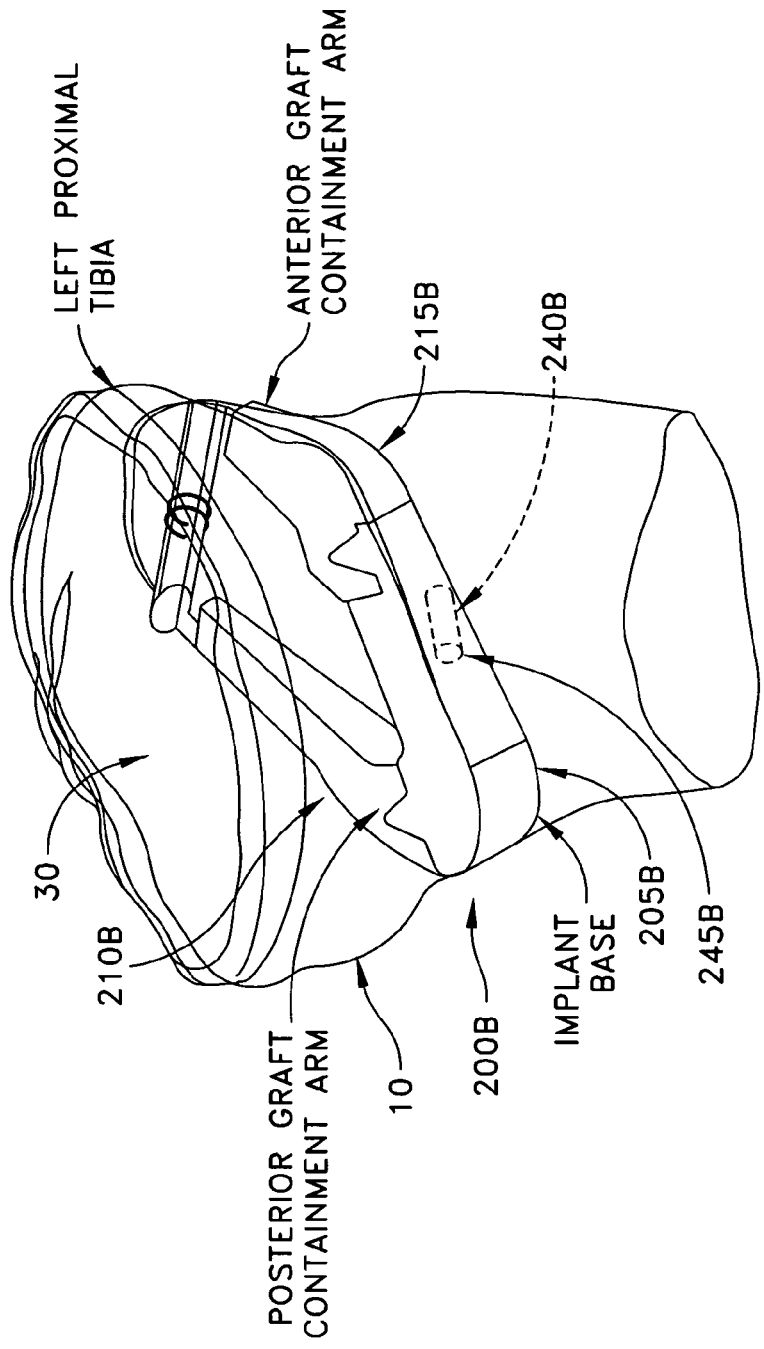
Figure 16:
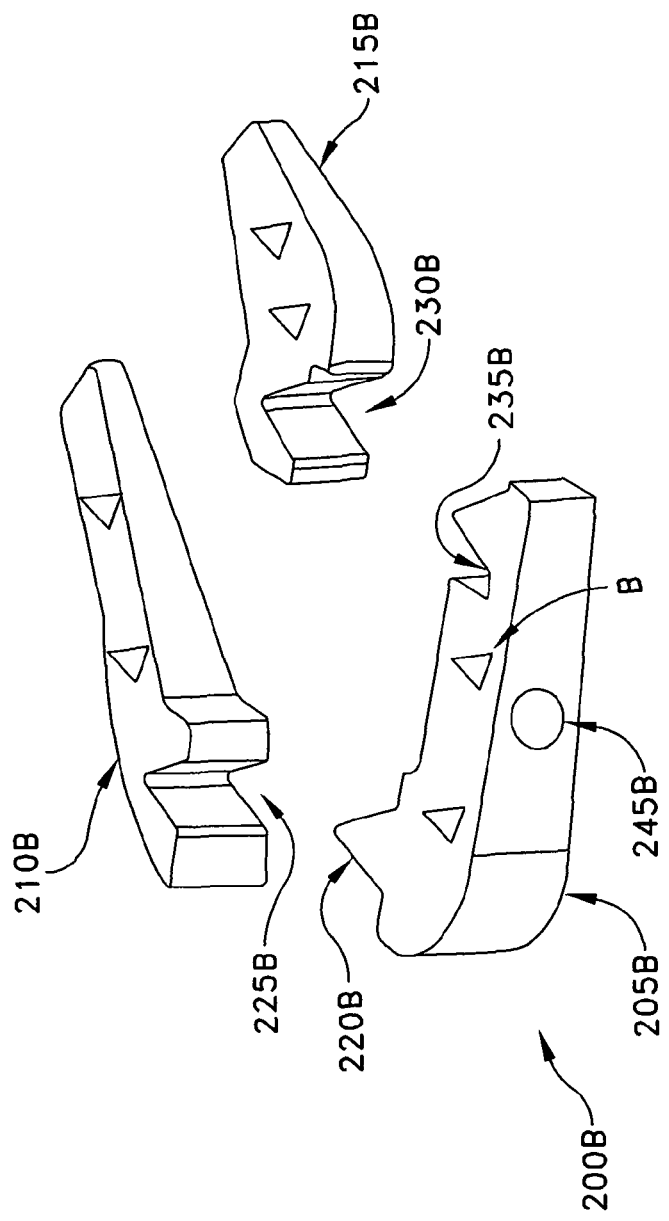
Figure 17:
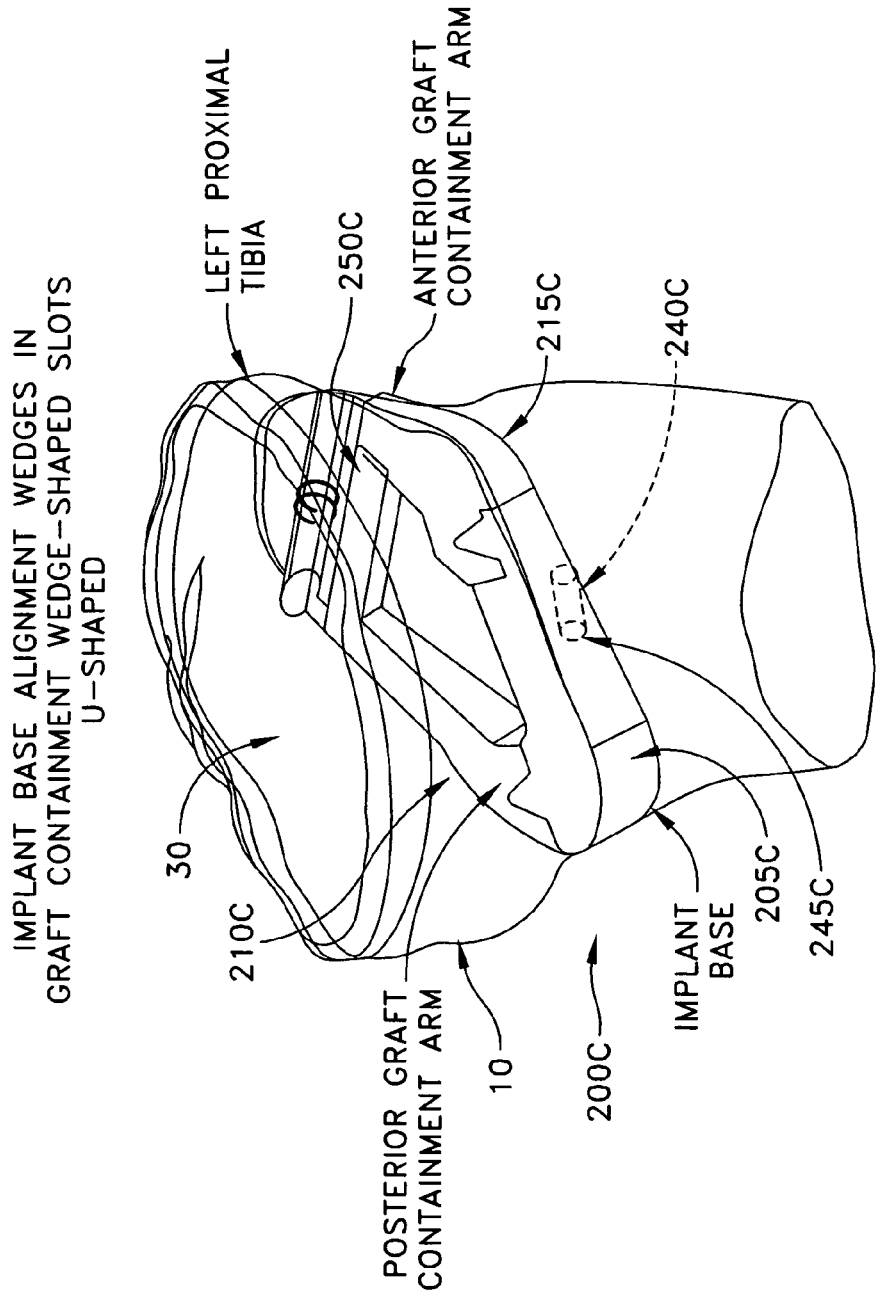
Figure 18:
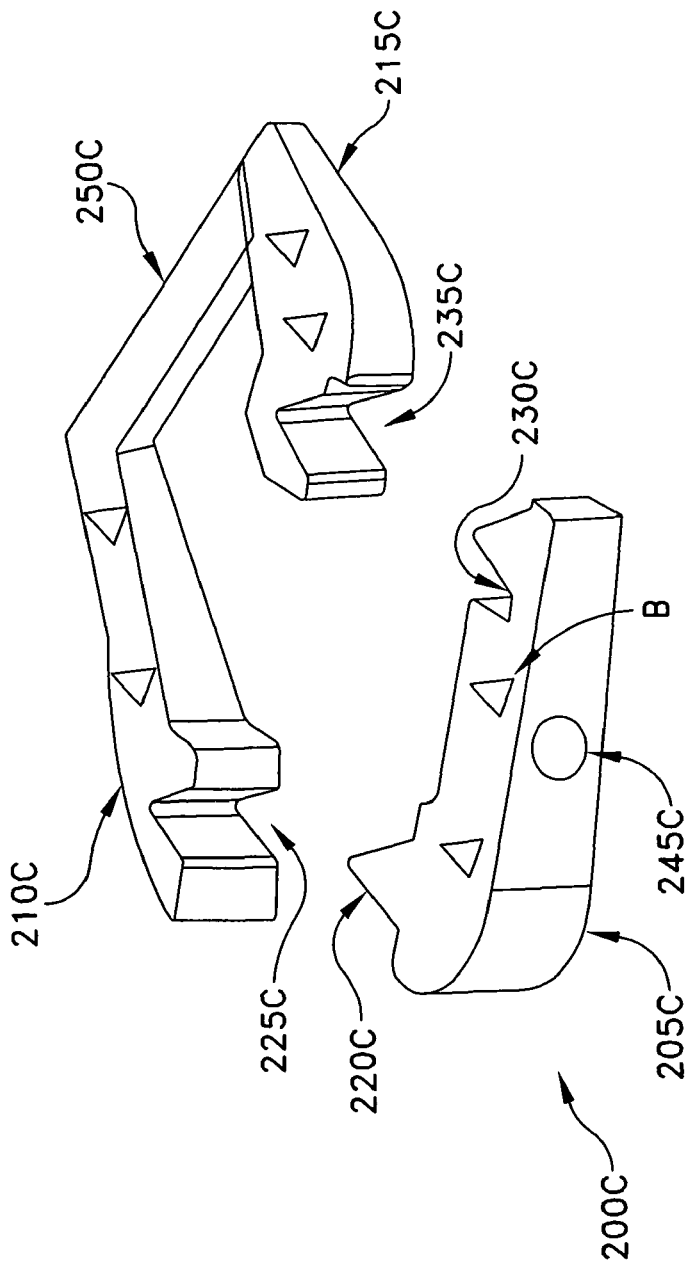

And with the novel implant 200 shown in FIGS. 11 and 12, first graft containment arm 210 and second graft containment arm 215 could each be provided with multiple wedges, etc.; with novel implant 200A shown in FIGS. 13 and 14, first graft containment arm 210A and second graft containment arm 215A could each be provided with multiple wedges, etc.; with novel implant 200B shown in FIGS. 15 and 16, first graft containment arm 210B and second graft containment arm 215B could each be provided with multiple grooves, etc.; with the novel implant 200C shown in FIGS. 17 and 18, first graft containment arm 210C and second graft containment arm 215C could each be provided with multiple grooves, etc.

And with the novel implants 400, 400A, 400B and 400C, shown in FIGS. 27-28, 29-30, 31-32 and 33-34, respectively, multiple flat surfaces, set at various angles, may be provided on the elements.

In addition, where a graft containment arm has multiple connector elements thereon, those connector elements may be a combination of male (e.g., tab, wedge, ball, etc.), female (e.g., slot, groove, socket, etc.) and/or flat connectors.

Furthermore, the particular angles at which tabs, slots, wedges, grooves, flat surfaces, etc. are disposed may be varied as appropriate.

MATERIALS

It should be appreciated that the aforementioned implants may be formed out of various metals (e.g., titanium, stainless steel, etc.) or other biocompatible materials, including polymers, with the materials being absorbable or non-absorbable, osteoinductive or osteoconductive, etc.

Furthermore, it should be appreciated that different components of the multi-part implant may be formed out of different materials, depending on the function of the components. By way of example but not limitation, different components may have different formulations so as to provide different strength characteristics, different absorption rates, etc.

MODIFICATIONS

It will be understood that many additional changes in the details, materials, steps and arrangements of parts, which have been herein described and illustrated in order to explain the nature of the invention, may be made by those skilled in the art within the principles and scope of the invention as expressed in the appended claims.

What is claimed is:

1. A method for conducting an open wedge osteotomy, the method comprising:
   forming a wedge-like opening in a bone defined by a top surface of the bone, a bottom surface of the bone, and distal apex surface, the wedge-shaped opening having a first open side, a second open side, and a base open side;
   positioning a first implant arm along the first open side;
   positioning a second implant arm along the second open side wherein the first implant arm is longer than the second implant arm;
   positioning a base wedge component within the wedge-like opening; and
   connecting the base wedge component to the first and second implant arms to form an osteotomy implant.

2. A method according to claim 1, wherein the base wedge component is connected to the first implant arm and second implant arm by a tab and slot interface connection.

3. A method according to claim 2, wherein the osteotomy wedge is configured to be deployed with an antero-medial approach, with the first implant arm being disposed in the posterior position, the second implant arm being disposed in the anterior position, and the base wedge component being disposed in the antero-medial position.

4. A method according to claim 3, wherein the osteotomy wedge defines an interior recess for receiving at least one of bone paste, bone cement and other bone graft materials.

5. A method according to claim 4, wherein the first implant arm and second implant arm are connected by a bridge.

6. A method according to claim 1, wherein the base wedge component is connected to the first implant arm and second implant arm by multiple tab and slot interface connections.

7. A method according to claim 1, wherein the base wedge component is connected to the first implant arm and second implant arm by a wedge and groove interface connection.

8. A method according to claim 7, wherein the osteotomy wedge is configured to be deployed with an antero-medial approach, with the first implant arm being disposed in the posterior position, the second implant arm being disposed in the anterior position, and the base wedge component being disposed in the antero-medial position.

9. A method according to claim 8, wherein the osteotomy wedge defines an interior recess for receiving at least one of bone paste, bone cement and other bone graft materials.

10. A method according to claim 9, wherein the first implant aim and second implant arm are connected by a bridge.

11. A method according to claim 1, wherein the base wedge component is connected to the first implant aim and second implant arm by multiple wedge and groove interface connections.

12. A method according to claim 1, wherein the base wedge component is connected to the first implant arm and second implant aim by a ball and socket interface connection.

13. A method according to claim 12, wherein the osteotomy wedge is configured to be deployed with an antero-medial approach, with the first implant arm being disposed in the posterior position, the second implant arm being disposed in the anterior position, and the base wedge component being disposed in the antero-medial position.

14. A method according to claim 13, wherein the osteotomy wedge defines an interior recess for receiving at least one of bone paste, bone cement and other bone graft materials.

15. A method according to claim 14, wherein the first implant arm and second implant arm are connected by a bridge.

16. A method according to claim 1, wherein the base wedge component is connected-to the first implant arm and second implant arm by a flat-to-flat interface connection.

17. A method according to claim 16, wherein the osteotomy wedge is configured to be deployed with an antero-medial approach, with the first implant atm being disposed in the posterior position, the second implant arm being disposed in the anterior position, and the base wedge component being disposed in the antero-medial position.

18. A method according to claim 17, wherein the osteotomy wedge defines an interior recess for receiving at least one of bone paste, bone cement and other bone graft materials.

19. A method according to claim 18, wherein the first implant arm and second implant arm are connected by a bridge.

20. A method according to claim 1, wherein the base wedge component is connected to the first implant arm and second implant arm by multiple flat-to-flat interface connections.

21. A method for conducting an open wedge osteotomy, the method comprising:
   forming a wedge-like opening in a bone to form upper and lower wedge surfaces;
   providing a multi-part wedge-shaped structure including at least a base wedge component to engage the upper and lower wedge surfaces, a first arm, and a second arm wherein the first arm is longer than the second arm;
   positioning the multi-part wedge-shaped structure within the wedge-like opening; and
   attaching the base component to the first arm and the second arm.

22. A method according to claim 21 further comprising passing at least one screw through the wedge-shaped structure and into the tibia so as to further secure the wedge-shaped structure within the wedge-like opening.

23. A method according to claim 21, further comprising assembling the at least base wedge component, first wedge arm, and second wedge arm in situ within the wedge-like opening.

24. A method according to claim 21, wherein the base wedge component has a plurality of engagement enhancers to engage with at least one of the upper and lower wedge surfaces.

25. A method for conducting an open wedge osteotomy, the method comprising:
   forming a wedge-like opening in a bone;
   positioning a first implant arm along a first side of the wedge-like opening;
   positioning a second implant arm along a second side of the wedge-like opening wherein the first implant arm is longer than the second implant arm; and
   subsequently inserting and connecting a base wedge component to the first and second implant arms within the wedge-like opening such that the first implant arm, second implant arm, and base wedge component form a U-shaped perimeter.

* * * * *